(12) United States Patent
Bringhurst et al.

(10) Patent No.: US 7,033,773 B1
(45) Date of Patent: Apr. 25, 2006

(54) SCREENING ASSAYS FOR G PROTEIN COUPLED RECEPTOR AGONISTS AND ANTAGONISTS

(75) Inventors: F. Richard Bringhurst, Walpole, MA (US); Hisashi Takasu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/696,982

(22) Filed: Oct. 27, 2000

Related U.S. Application Data

(63) Continuation of application No. 08/903,977, filed on Jul. 31, 1997, now Pat. No. 6,183,974.

(51) Int. Cl.
*G01N 33/567* (2006.01)

(52) U.S. Cl. ...................................... 435/7.21; 436/501
(58) Field of Classification Search ................ 435/7.21, 435/701; 437/7, 7.2; 432/702
See application file for complete search history.

(56) References Cited

U.S. PATENT DOCUMENTS

| 5,462,856 A | 10/1995 | Lerner et al. | 435/7.21 |
| 5,494,806 A | 2/1996 | Segre et al. | 435/69.1 |

FOREIGN PATENT DOCUMENTS

| AU | 668118 | 6/1993 |
| WO | WO 93/11257 | 6/1993 |

OTHER PUBLICATIONS

Strathman, et al., "G protein diversity: A distinct class of α subunits is present in vertebrates and invertebrates," *Proc. Natl. Acad. Sci.* 87:9113–9117, The National Academy of Sciences of the USA (1990).

Pang, et al., "Purification of Unique α Subunits of GTP-binding Regulatory Proteins (G Proteins) by Affinity Chromatography with Immobilized βγ Subunits," *J. of Biol. Chem.* 265: 18707–18712, The American Society for Biochemistry and Molecular Biology, Inc. (1990).

Abou–Samra, A.B., et al., "Cyclic Adenosine 3', 5'–Monophosphate (cAMP)–Dependent and cAMP–Independent Regulation of Parathyroid Hormone Receptors on UMR 106–01 Osteoblastic Osteosarcoma Cells," *Endocrinology* 129:2547–2554, The Endocrine Society (1991).

Abou–Samra, A.–B., et al., "Expression cloning of a common receptor for parathyroid hormone and parathyroid hormone–related peptide from rat osteoblast–like cells: A single receptor stimulates intracellular accumulation of both cAMP and inositol triphosphates and increases intracellular free calcium," *Proc. Natl. Acad. Sci. USA* 89:2732–2736, The National Academy of Sciences of the USA (1992).

Abou–Samra, A.B., et al., "Down–Regulation of Parathyroid (PTH)/PTH–Related Peptide Receptor Immunoreactivity and PTH Binding in Opossum Kidney Cells by PTH and Dexamethasone," *Endocrinology* 135:2588–2594, The Endocrine Society (1994).

Adams, A.E., et al., "Probing the Bimolecular Interactions of Parathyroid Hormone and the Human Parathyroid Hormone/Parathyroid Hormone–Related Protein Receptor. 2. Cloning, Characterization, and Photoaffinity Labeling of the Recombinant Human Receptor," *Biochemistry* 34:10553–10559, The American Chemical Society (1995).

Azarani, A., et al., "Parathyroid Hormone and Parathyroid Hormone–related Peptide Activate the $Na^+H^+$ Exchanger NHE–1 Isoform in Osteoblastic Cells (UMR–106) via a cAMP–dependent Pathway," *J. Biol. Chem.* 270:23166–23172, The American Society for Biochemistry and Molecular Biology, Inc. (1995).

Azarani, A., et al., "Structurally Diverse N–terminal Peptides of Parathyroid Hormone (PTH) and PTH–related Peptide (PTHRP) Inhibit the $Na^+/H^+$ Exchanger NHE3 Isoform by Binding to the PTH/PTHRP Receptor Type I and Activating Distinct Signaling Pathways," *J. Biol. Chem.* 271:14931–14936, The American Society for Biochemistry and Molecular Biology, Inc. (Jun. 1996).

Bringhurst, F.R., et al., "Cloned, Stably Expressed Parathyroid Hormone (PTH)/PTH–Related Peptide Receptors Activate Multiple Messenger Signals and Biological Responses in LLC–$PK_1$ Kidney Cells," *Endocrinology* 132:2090–2098, The Endocrine Society (1993).

Catanzariti, L. et al., "A Novel Expression System for $G_S$–Coupled Receptors," *BioTechniques* 15:474–479, Eaton Publishing Co. (1993).

Chakravarthy, B.R., et al., "Parathyroid Hormone Fragment [3–34] Stimulates Protein Kinase C (PKC) Activity in Rat Osteosarcoma and Murine T–Lymphoma Cells," *Biochem. Biophys. Res. Commun.* 171:1105–1110, Academic Press, Inc. (1990).

Civitelli, R., et al., "Parathyroid Hormone–Related Peptide Transiently Increases Cytosolic Calcium in Osteoblast–Like Cells: Comparison with Parathyroid Hormone," *Endocrinology* 125:1204–1210, The Endocrine Society (1989).

Dempster, D.W., et al., "Anabolic Actions of Parathyroid Hormone on Bone," *Endocrine Rev.* 14:690–709, The Endocrine Society (1993).

(Continued)

*Primary Examiner*—John Ulm
(74) *Attorney, Agent, or Firm*—Sterne Kessler Goldstein & Fox P.L.L.C.

(57) ABSTRACT

Parathyroid hormone (PTH) and its closely related peptide, PTHrP, share the same receptor, PTHR. LLC-PK1 cells are porcine renal epithelial cells which do not normally express PTHR. The present-invention provides stably transfected LLC-PK1 cells which express human PTHR. Also provided are methods for determining whether a compound of interest is an agonist or antagonist of a Gs or Gq protein coupled receptor.

12 Claims, 11 Drawing Sheets

OTHER PUBLICATIONS

Dohlman, H.G., et al., "Model Systems for the Study of Seven–Transmembrane–Segment Receptors," *Annu. Rev. Biochem. 60*:653–688, Annual Reviews Inc. (1991).

Dunlay, R., and Hruska, K., "PTH receptor coupling to phospholipase C is an alternate pathway of signal transduction in bone and kidney," *Am. J. Physiol. 258*:F223–F231, The American Physiological Society (1990).

Freyaldenhoven, A.M., et al., "Protein kinase C differentially modulaes PTH– and $PGE_2$–sensitive adenylate cyclase in osteoblast–like cells," *Am. J. Physiol. 262*:E87–E95, The American Physiological Society (1992).

Fujimori, A., et al., "Dissociation of Second Messenger Activation by Parathyroid Hormone Fragments in Osteosarcoma Cells," *Endocrinology 128*:3032–3039, The Endocrine Society (1991).

Fujimori, A., et al., "Structure–Function Relationship of Parathyroid Hormone: Activation of Phospholipase–C, Protein Kinase–A and –C in Osteosarcoma Cells," *Endocrinology 130*:29–36, The Endocrine Society (1992).

Fukayama, S., et al., "Mechanisms of Desensitization to Parathyroid Hormone in Human Osteoblast–Like SaOs–2 Cells," *Endocrinology 131*:1757–1769, The Endocrine Society (1992).

Fukayama, S., et al., "Role of Protein Kinase–A in Homologous Down–Regulation of Parathyroid Hormone (PTH)/PTH–Related Peptide Receptor Messenger Ribonucleic Acid in Human Osteoblast–Like SaOS–2 Cells," *Endocrinology 134*:1851–1858, The Endocrine Society (1994).

Guo, J., et al., "Parathyroid Hormone (PTH)/PTH–Related Peptide Receptor Density Modulates Activation of Phospholipase C and Phosphate Transport by PTH in LLC–PK1 Cells," *Endocrinology 136*:3884–3891, The Endocrine Society (1995).

Jans, D.A., and Hemmings, B.A., "LLC–$PK_1$ cell mutants in cAMP metabolism respond normally to phorbol esters," *FEBS Lett. 205*:127–131, Elsevier Science B.V. (1986).

Janulis, M., et al., "Structure–Function Requirements of Parathyroid Hormone for Stimulation of 1,25–Dihydroxyvitamin $D_3$ Production by Rat Renal Proximal Tubules," *Endocrinology 133*:713–719, The Endocrine Society (1993).

Jouishomme, H., et al., "The Protein Kinase–C Activation Domain of the Parathyroid Hormone," *Endocrinology 130*:53–60, The Endocrine Society (1992).

Jüppner, H., et al., "A G Protein–Linked Receptor for Parathyroid Hormone and Parathyroid Hormone–Related Peptide," *Science 254*:1024–1026, American Association for the Advancement of Science (1991).

Kaufmann, M., et al., "Functional expression of a stably transfected parathyroid hormone/parathyroid hormone related protein receptor complementary DNA in CHO cells," *Mol. Cell. Endocrinol. 104*:21–27, Elsevier Science Ireland Ltd. (1994).

Menniti, F.S., et al., "Different Modes of Regulation for Receptors Activating Phospholipase C in the Rat Pancreatoma Cell Line AR4–2J," *Mol. Pharmacol. 40*:727–733, The American Society for Pharmacology and Experimental Therapeutics (1991).

Mitchell, J., and Goltzman, D., "Mechanisms of Homologous and Heterologous Regulation of Parathyroid Hormone Receptors in the Rat Osteosarcoma Cell Line UMR–106," *Endocrinology 126*:2650–2660, The Endocrine Society (1990).

Neugebauer, W., et al., "Solution Structure and Adenylyl Cyclase Stimulating Activities of C–Terminal Truncated Human Parathyroid Hormone Analogues," *Biochemistry 34*:8835–8842, American Chemical Society (1995).

Pines, M., et al., "Generation and Characterization of Human Kidney Cell Lines Stably Expressing Recombinant Human PTH/PTHrP Receptor: Lack of Interaction with a C–Terminal Human PTH Peptide," *Endocrinology 135*:1713–1716, The Endocrine Society (1994).

Pines, M., et al., "Inositol 1–,4–,5–Trisphosphate–Dependent $Ca^{2+}$ Signaling by the Recombinant Human PTH/PTHrP Receptor Stably Expressed in a Human Kidney Cell Line," *Bone 18*:381–389, Elsevier Science Inc. (Apr. 1996).

Reid, I.R., et al., "Parathyroid hormone acutely elevates intracellular calcium in osteoblastlike cells," *Am. J. Physiol. 253*:E45–E51, The American Physiological Society (1987).

Rixon, R.H., et al., "Parathyroid Hormone Fragments May Stimulate Bone Growth in Ovariectomized Rats by Activating Adenylyl Cyclase," *J. Bone Miner. Res. 9*:1179–1189, Mary Ann Liebert, Inc. (1994).

Schipani, E., et al., "A Constitutively Active Mutant PTH–PTHrP Receptor in Jansen–Type Metaphyseal Chondrodysplasia," *Science 268*:98–100, American Association for the Advancement of Science (1995).

Schneider, H., et al., "Cloning and functional expression of a human parathyroid hormone receptor," *Eur. J. Pharmacol.—Mol. Pharmacol. Sect. 246*:149–155, Elsevier Science B.V. (1993).

Schneider, H., et al., "A C–terminally truncated human parathyroid hormone receptor is functional and activates multiple G proteins," *FEBS Lett. 351*:281–285, Elsevier Science B.V. (1994).

Shukunami, C., et al., "Chondrogenic Differentiation of Clonal Mouse Embryonic Cell Line ATDC5 In Vitro: Differentiation–dependent Gene Expression of Parathyroid Hormone (PTH)/PTH–related Peptide Receptor," *J. Cell Biol. 133*:457–468, The Rockefeller University Press (Apr. 1996).

Simon, M.I., et al., "Diversity of G Proteins in Signal Transduction," *Science 252*:802–808, American Association for the Advancement of Science (1991).

Takasu, H. et al., "Dual Signaling and Ligand Selectivity of the Human PTH/PTHrP Receptor," *J. Bone & Mineral Res. 14*:11–20, American Society for Bone and Mineral Research (Jan. 1999).

Ullrich, A., and Schlessinger, J., "Signal Transduction by Receptors with Tyrosine Kinase Activity," *Cell 61*:203–212, Cell Press (1990).

Whitfield, J.F., and Morley, P., "Small bone–building fragments of parathyroid hormone: new therapeutic agents for osteoporosis," *Trends Pharmacol. Sci. 16*:382–386, Elsevier Science Ltd (1995).

Yamaguchi, D.T., et al., "Parathyroid Hormone–activated Calcium Channels in an Osteoblast–like Clonal Osteosarcoma Cell Line: cAMP–dependent and cAMP–independent Calcium Channels," *J. Biol. Chem. 262*:7711–7718, The American Society of Biological Chemists, Inc. (1987).

Yamamoto, I., et al., "Characterization and Agonist–Induced Down–Regulation of Parathyroid Hormone Receptors in Clonal Rat Osteosarcoma Cells," *Endocrinology 122*:1208–1217, The Endocrine Society (1988).

Co–Pending U.S. Appl. No. 08/903,977, Bringhurst et al. filed Jul. 31, 1997.

SCREENING ASSAYS FOR G PROTEIN COUPLED RECEPTOR AGONISTS AND ANTAGONISTS

This Application is a continuation of U.S. application Ser. No. 08/903,977, filed on Jul. 31, 1997, which is now U.S. Pat. No. 6,183,974, which relied upon and is fully incorporated by reference herein.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates to G protein coupled receptors. More specifically, screening assays for Gs and Gq protein coupled receptor agonists and antagonists are provided. Also provided are stably transfected cell lines.

2. Related Art

Parathyroid hormone (PTH) is a major systemic regulator of bone turnover, and the closely related peptide, PTHrP, which is widely expressed in adult and fetal tissues, is believed to exert important paracrine actions, especially in developing cartilage and bone (Dempster, D. W., et al., *Endocrine Rev* 14:690–709 (1993); Lanske, B., et al., *Science* 273:663–666 (1996); Lee, K., et al., *Endocrinology* 137:5109–5118 (1996); Rixon, R. H., et al., *J Bone Miner Res* 9:1179–1189 (1994)). Exogenously administered PTH exerts striking effects upon bone mass in vivo, the nature of which depends critically upon the dose of PTH and the resulting temporal profile of the concentration of circulating peptide (Dempster, D. W., et al., *Endocrine Rev* 14:690–709 (1993)). Thus, continuous exposure to high PTH concentrations leads to net bone resorption and osteopenia, whereas intermittent administration of low doses leads to increased net bone formation—a finding that has fueled great interest in the possible use of PTH, or PTH analogs, as anabolic agents to increase bone mass and to prevent or treat metabolic bone diseases, including osteoporosis (Dempster, D. W., et al., *Endocrine Rev* 14:690–709 (1993), whitfield, J. F., and Morley, P., *Trends Pharmacol Sci* 16:382–386 (1995)).

Both PTH and PTHrP can activate a single receptor, the PTH/PTHrP receptor (PTHR), which has been cloned from several species, including rat, opossum, mouse, pig and human, and shown to be expressed in cells of bone (Abou-Samra, A. B., et. al., *Proc Natl Acad Sci USA* 89:2732–2736 (1992); Juppner, H., et al., *Science* 254:1024–1026 (1991); Schneider, H., *Eur J Pharmacol* 246:149–155 (1993); Bringhurst, F. R., et al., *Endocrinology* 132:2090–2098 (1993); Pines, M., et al., *Endocrinology* 135:1713–1716 (1994)). Activation of the PTHR in osteoblasts evokes multiple parallel signaling events, including activation of adenylyl cyclase (AC), phospholipase C (PLC) and cytosolic free calcium transients (Abou-Samra, A. B., et al., *Proc Natl Acad Sci USA* 89:2732–2736 (1992), Juppner, H., et al., *Science* 254:1024–1026 (1991), Bringhurst, F. R., et al., *Endocrinology* 132:2090–2098 (1993), Dunlay, R., and Hruska, K., *Am J Physiol* 258:F223–231 (1990); Fujimori, A., et al., *Endocrinology* 128:3032–3039 (1991); Yamaguchi, D. T., et al., *J Biol Chem* 262:7711–7718 (1987)). The links between each of these individual signaling events and the ultimate integrated tissue responses to PTH, such as changes in overall bone mass, remain largely undefined. It has been reported that PTH analogs which appear to selectively activate AC can generate a full anabolic effect on bone following intermittent administration in vivo (Rixon, R. H., et al., *J Bone Miner Res* 9:1179–1189 (1994), Whitfield, J. F., and Morley, P., *Trends Pharmacol Sci* 16:382–386 (1995), Whitfield, J. F., et al., *Calcif Tissue Int* 58:81–87 (1996)). Such observations have suggested that individual PTH second messengers may indeed be linked to specific tissue responses and, therefore, that the pattern of PTHR signaling events, as well as their intensity, may dictate both the qualitative and quantitative aspects of the response in bone. The issue is complicated by the fact that, in bone, mature osteoclasts are believed not to express PTHRs and thus must experience these influences of PTH only indirectly via responses generated by adjacent cells, such as osteoblasts or marrow stromal cells, which do express these receptors (Dempster, D. W., et al., *Endocrine Rev* 14:690–709 (1993), McSheehy, P., and Chambers, T., *Endocrinology* 118:824–828 (1986)). The manner whereby such osteoblastic or stromal PTH target cells might convey, to neighboring cells of the osteoclastic lineage, complex information reflecting subtle differences in temporal and concentration profiles of PTH exposure remains obscure.

Striking desensitization and downregulation of PTHRs has been described following exposure to high concentrations of ligand (Fujimori, A, et al., *Endocrinology* 128:3032–3639 (1991), Abou-Samra, A-B, et al., *Endocrinology* 129:2547–2554 (1991); Mitchell, J., and Goltzman, D., *Endocrinology* 126:2650–2660 (1990); Fukayama, S., et al., *Endocrinology* 131:1757–1769 (1992)) and it was reported recently that the pattern of signaling events generated by the rat PTHR is strongly influenced by the level of its expression on the cell surface (Guo, J., et al., *Endocrinology* 136:3884–3891 (1995)). Specifically, it was found that the magnitude of the PLC response was directly related to the density of available PTHRs on the surface of stably transfected LLC-PK1 cells across a range of expression (40,000–300,000 receptors per cell) that did not affect the maximal AC response (Guo, J., et al., *Endocrinology* 136:3884–3891 (1995)).

The human PTHR has been expressed previously in cultured cells (Pines, M., et al., *Endocrinology* 135:1713–1716 (1994), Schneider, H., et al., *FEBS Lett* 351:281–285 (1994), Pines, M., et al., *Bone* 18:381–389 (1996)), but its signaling properties have not yet been elucidated fully. In particular, the effects of alterations in human PTHR expression on the character of the signal transduction response(s) have not been systematically analyzed. Certain amino- or carboxyl-terminally truncated PTH analogs, such as PTH(3-34), PTH(7-34) and PTH(1-31), have been previously found to exhibit selective activation of only a subset of the usual PTHR second messengers (Rixon, R. H., et al., *J Bone Miner Res* 9:1179–1189 (1994), Whitfield, J. F., and Morley, P., *Trends Pharmacol Sci* 16:382–386 (1995), Fujimori, A., et al., *Endocrinology* 128:3032–3039 (1991), Abou-Samra, A. B., et al., *Endocrinology* 135:2588–2594 (1994), Azarani, A., et al., *J Biol Chem* 271:14931–14936 (1996); Chakravarthy, B. R., et al., *Biochem Beefiest Res Commum* 171:1105–1110 (1990); Fujimori, A., et al., *Endocrinology* 130:29–36 (1992); Jouishomme, H., et al., *Endocrinology* 130:53–60 (1992); Janulis, M., et al., *Endocinology* 133:713–719 (1993)). The hPTH(1-31) analog was reported to activate AC but not PKC and yet to retain striking anabolic effects in ovariectomized rats (Rixon, R. H., et al, *J Bone Miner Res* 9:1179–1189 (1994), Jouishomme, H., et al., *J Bone Miner Res* 9:943–949

(1994)). Confirmation of such selective signaling via human PTHRs would provide important additional rationale for the development of these signal-specific PTH peptides for clinical use. Thus, there is a need in the art for characterization of responses mediated by PTHR.

SUMMARY OF THE INVENTION

The present inventors isolated and characterized numerous subclones of the well-characterized renal epithelial LLC-PK1 cell line that collectively expressed a broad range of stable transfected human PTHRs. It was found that, as with the rat PTHR, the human receptor activates AC maximally at levels of receptor expression far lower than those needed for PLC activation. Further, the temporal pattern and magnitude of PLC activation in these cells is strongly dependent upon the density of cell-surface human PTHRs across a range of expression above that which elicits maximal AC activation. Surprisingly, it was also found that hPTH(1-31) and hPTH(1-34) activate PLC and cytosolic free calcium transients equivalently via the human PTHR and, moreover, that hPTH(1-31) fully induces other, more delayed biologic responses to PTH in these cells that depend upon cAMP-independent signaling pathways. These findings point to a potential physiologic role of PTHR regulation and differential signaling in fashioning the integrated cellular response in tissues such as bone or kidney, and they indicate that the ligand selectivity of human PTHRs may differ from that of other species of PTHRs.

The present inventors also have developed a convenient and sensitive spectrophotometric bioassay that responds to activation of either AC or PLC via the human PTHR in these cells, and have employed it, together with other measurements, to show that analogs such as PTH(3-34) and PTH(1-31), previously found to be signal-selective agonists in rat cells, may exhibit different spectra of biologic activities via the human PTHR.

Thus, the present invention provides a stably transfected cell line comprising LLC-PK1 cells which express PTHR.

The present invention also provides a method for determining whether a compound of interest is an agonist or antagonist of a Gs or Gq protein coupled receptor comprising:
(a) providing a cell line which expresses urokinase-type plasminogen activator (u-PA);
(b) providing an expression vector comprising a nucleotide sequence encoding for a Gs or Gq protein coupled receptor, said receptor not normally expressed in said cell line of step (a);
(c) introducing said expression vector into said cell line, thereby providing stably transfected cells;
(d) contacting said stably transfected cells with said compound of interest; and
(e) measuring the u-PA activity of the cell culture supernatant of said cells of step (d).

The present invention further comprises a method of determining whether a compound of interest is an agonist or antagonist of a Gs or Gq coupled receptor using LLC-PK1 cells in the above-described method. The present invention further provides a method of determining whether a compound of interest is an agonist or antagonist of human PTHR using the above-described method.

BRIEF DESCRIPTION OF THE FIGURES

FIG. 2A shows the responses to hPTH(1-34), at the indicated concentrations, in HKRK B7 cells (●; 950,000 receptors per cell) and HKRK B28 cells (○; 280,000 receptors per cell). FIG. 2B shows the responses in HKRK B28 cells to: hPTH(1-34) (○), hPTH(1-31) (Δ), hPTH(3-34) (■), hPTH(7-34) (□), hPTHrp(1-36) (◆), and sCT (▲). Results were expressed as fold basal. Each point represents the mean±SEM of triplicate determinations.

FIG. 4A shoes HKRK B7 cells (●) and HKRK B28 cells (○) that were stimulated with hPTH(1-34) (1000 nM) for the indicated time. FIG. 4B shows cells that were stimulated with hPTH(1-34) at the indicated concentrations for 30 min (HKRK B7) or 4 min (HKRK B28). Results are expressed as percent of basal, and each point is the mean±SEM of three experiments performed in triplicate.

DETAILED DESCRIPTION OF THE PREFERRED EMBODIMENTS

Figure 1A:
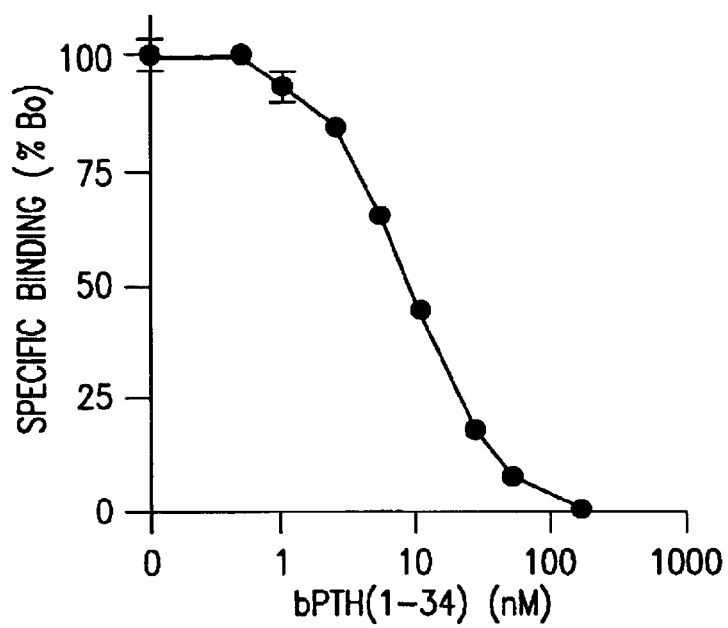
FIGS. 1A–1B and 1C–1D. Competitive radioligand binding to human PTH/PTHrp receptors stably expressed in LLC-PK1 cells. LLC-PK1 cells stably expressing (FIGS. 1A–1B) 950,000 receptors/cell (HKRK B7) or (FIGS. 1C–1D) 280,000 receptors/cell (HKRK B28) were incubated with $^{125}$I-[Nle$^{8,18}$,Tyr$^{34}$]bPTH(1-34) in binding buffer for 6 hr at 15° C. in the presence or absence of increasing concentrations of nonradioactive ligand. Scatchard plots are shown in the insets. Each point represents the mean± of triplicate determinations. Total radioligand bound ranged from 15,000–30,000 cpm/well, and nonspecific binding was 2–5% of total binding.
Figure 1B:
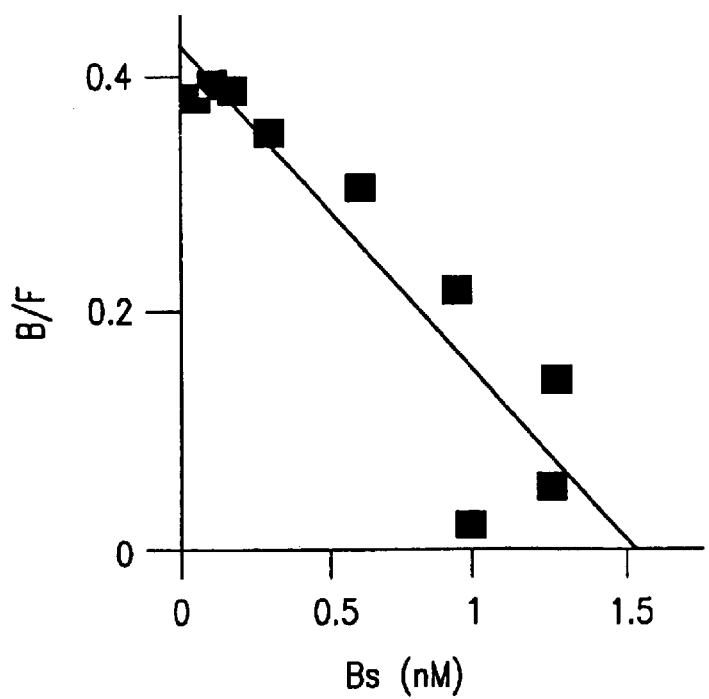
Figure 1C:
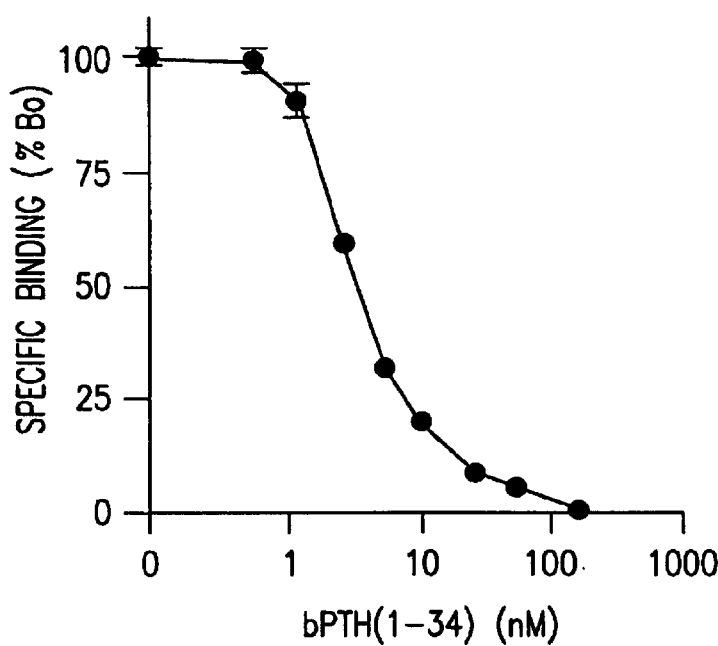
Figure 1D:
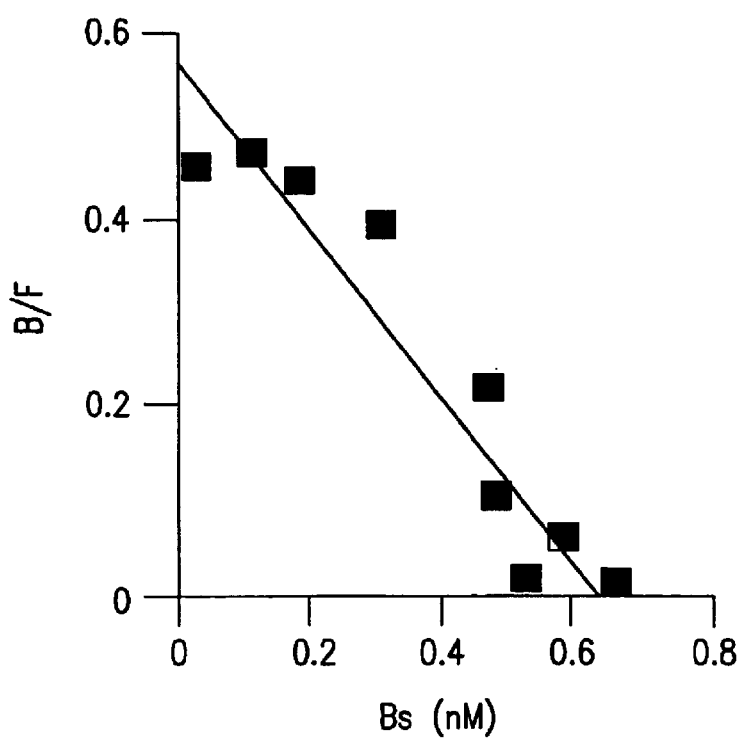

The present inventors have developed LLC-PK1 cell lines which express human PTHR The present studies of clonal LLC-PK1 cell lines that collectively span a broad range of expression of stably transfected human PTHRs have demonstrated receptor density-dependent differences in hPTH signaling and biologic activity that indicate an important role for regulation of human receptor expression in modulating the character, as well as the magnitude, of the cellular response to the hormone.

In one embodiment of the present invention, a stably transfected cell line is provided comprising LLC-PK1 cells which express human PTHR. A cell line is a population of cells of the same type that is capable of indefinite survival in culture. By "stably transfected cell line" it is meant that the cell line has been altered in some way to express a polypeptide which it does not normally express. By "express" it is meant that a structural gene is transcribed into mRNA and that such mRNA is translated to produce a polypeptide. LLC-PK1 cells are porcine renal epithelial cells which express calcitonin and vasopressin receptors, but do not normally express PTHR and are available from the American Type Culture Collection, ATCC No. CL-101. The human PTHR is a receptor which binds to both human PTH and human PTHrP. The human PTHR has been previously cloned (Schneider et al., *Eur. J. Pharmacol.* 246:149–155 (1993); Adams et al., *Biochem.* 34:10553–10559 (1995)). Thus, LLC-PK1 cells which express human PTHR are said to be "stably transfected."

It has previously been shown that u-PA is secreted by LLC-PK1 cells in response to activation of both the PKA and PKC pathways by calcitonin (Jans, D. A., and Hemmings, B. A., *FEBS Lett* 205:127–131 (1986)). The present inventors have reconfirmed that, in LLC-PK1 cells, both the PKA and PKC pathways are linked to u-PA production. The present inventors have developed a spectrophotometric bioassay that measures u-PA production, and thus PKA or PKC activation, in these cells. An agonist of a Gs or Gq protein coupled receptor increases u-PA production in cells which express u-PA. An antagonist of a Gs or Gq protein coupled receptor inhibits the activity of a Gs or Gq protein coupled receptor agonist, thereby decreasing u-PA production in cells which express u-PA relative to the agonist administered alone.

Cell lines other than LLC-PK1 express u-PA. These cell lines could be used to determine whether a compound is an agonist or antagonist of a Gs or Gq protein coupled receptor using the method of the present invention. Examples of cells lines which express u-PA include, but are not limited to, HE-LU (Rifkin) (ATCC No. CRL-7717); LLC-MK2 (ATCC No. CCL-7); NMU (ATCC No. CRL 1743); LLC-RK1 (ATCC No. CCL-106); and MIA PaCa-2 (CRL-1420).

Thus, a further embodiment of the present invention involves a method of determining whether a compound of interest is an agonist or antagonist of a Gs or Gq protein coupled receptor comprising: (a) providing a cell line which expresses urokinase-type plasminogen activator (u-PA); (b) providing an expression vector comprising a nucleotide sequence encoding for a Gs or Gq protein coupled receptor, said receptor not normally expressed in said cell line of step (a);(c) introducing said expression vector into said cell line, thereby providing stably transfected cells; (d) contacting said stably transfected cells with said compound of interest; and (e) measuring the u-PA activity of the cell culture supernatant of said cells of step (d). A preferred embodiment of the present invention is a method of determining whether a compound of interest is an agonist or antagonist of a Gs protein coupled receptor, using the above-described method. Another preferred embodiment of the present invention is a method of determining whether a compound of interest is an agonist or antagonist of a Gq protein coupled receptor, using the above-described method. An especially preferred embodiment of the present invention is a method of determining whether a compound of interest is a Gs or Gq protein coupled receptor agonist or antagonist using LLC-PK1 cells in the above-described method. Another especially preferred embodiment of the present invention is a method of determining whether a compound of interest is an agonist or antagonist of human PTHR using the above-described method.

A "compound of interest" could be a peptide, a polypeptide, a fragment of a polypeptide, an organic natural molecule, or a synthetic molecule. Examples of compounds that could be agonists or antagonists of Gs or Gq protein coupled receptors are hormones, hormone analogs, and antibodies.

An "agonist of a Gs or Gq protein coupled receptor" is a compound that interacts with a Gs or Gq protein coupled receptor and activates the Gs or Gq protein coupled receptor. An "antagonist of a Gs or Gq protein coupled receptor" is a compound that inhibits the agonist-induced activation of a Gs or Gq protein coupled receptor.

A "Gs or Gq protein coupled receptor" is a receptor that, when bound to its appropriate ligand, activates a Gs or Gq protein. Some receptors can activate both Gs and Gq proteins, while some activate only either Gs or Gq proteins. Preferably, the Gs or Gq protein coupled receptors used in the present invention should be capable of activating Gs or Gq proteins of the cells used in the method of the present invention. Examples of Gs protein coupled receptors include, but are not limited to, the β-adrenergic, glucagon, ADH, FSH, LH, and VIP receptors. Examples of Gq protein coupled receptors include, but are not limited to, the TRH, thrombin, and $PGF_{2\alpha}$ receptors. One example of a receptor which activates both Gs and Gq proteins is the calcitonin receptor.

As used herein, an "expression vector" is a vector comprising a structural gene operably linked to an expression control sequence so that the structural gene can be expressed when the expression vector is stably transfected into an appropriate host cell. Two DNA sequences are said to be "operably linked" if the nature of the linkage between the two nucleic acid molecules does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired nucleic acid sequence if the promoter were capable of effecting transcription of that nucleic acid sequence. Preferred promoters include the promoter of the mouse metallotionein I gene (Harner, D. et al., *J. Mol. Appl. Gen.* 1:273–288 (1982)), the HSV thymidine kinase promoter (McKnight, S. *Cell* 31:355–365 (1982)) or the SV40 early promoter (Benoist, C. et al., *Nature* 290:304–310 (1981)).

Expression of Gs or Gq protein coupled receptors in cells may be increased by inserting an enhancer sequence into the expression vector. Enhancers are cis-acting elements of DNA, generally about 10 to 300 bp in size, that act to increase transcriptional activity of a promoter. Illustrative examples of enhancers include, but are not limited to, the SV40 enhancer, which is located on the late side of the replication origin at bp 100 to 270; the cytomegalovirus early promoter enhancer; the polyoma enhancer on the late side of the replication origin; and adenovirus enhancers.

The expression vectors may provide for inducible expression of the nucleic acid sequence. Preferred among such vectors are vectors which provide for expression that is inducible by environmental factors that are easy to manipulate, such as temperature and nutrient additives.

The expression vectors may also contain a selectable marker for propagation in stably transfected cells. Representative examples of selectable markers include dihydrofolate reductase, hygromycin or neomycin resistance.

An expression vector can be provided commercially or it can be constructed through any method of cloning well-known in the art. Preferred expression vectors include, but are not limited to, pWLNEO, pSV2CAT, pOG44, pXT1, and pSG available from Stratagene; psVK3, pBPV, pMSG and pSVL available from Pharmacia; and pcDNAIneo available from Invitrogen. Other suitable vectors will be readily apparent to the skilled artisan.

The expression vector can be introduced into the host cell by any appropriate method, including infection, transduction, transfection, transvection, electroporation, and transformation. Such methods are described in many standard laboratory manuals, such as Davis et al., *Basic Methods in Molecular Biology* (1986).

By "not normally expressed in the cell line" it is meant that the Gs or Gq protein coupled receptor is not expressed at a detectable level in the cell line used in the method of the present invention.

By "contacting stably transfected cells with a compound of interest" it is meant that the compound of interest is administered to the stably transfected cells by any appropriate method. This can include administering the compound exogenously in vitro or in vivo, or further transfecting the cells to express the compound. When administering the compound exogenously, a carrier may be used. The carrier should be compatible with cell viability. Examples of carriers include, but are not limited to, DMSO, MeOH/EtOH, water, Tris, and HEPES.

The compound of interest may be highly purified, partially purified, or unpurified. Compounds of interest may be administered to the stably transfected cells alone or in combination. By administering the compounds in combination, synergistic effects on the Gs or Gq protein coupled receptor may be determined.

By "measuring the u-PA activity" it is intended qualitatively or quantitatively measuring or estimating the level of u-PA activity either directly (i.e., by determining orestimating absolute u-PA activity) or relatively (i.e., by comparing the u-PA activity of the stably transfected cell line that has been contacted with a compound of interest to a control stably transfected cell line that has not been contacted with the compound of interest). Preferably, the u-PA activity in the stably transfected cell line that has been contacted with a compound of interest will be compared to the u-PA activity of either the stably transfected cell line which has not been contacted with the compound of interest or an untransfected cell line which has been contacted with the same compound of interest, or both.

One preferred method of measuring u-PA activity is described in Example 3 below. Briefly, an aliquot of supernatant from stably transfected cells is transferred to a clean microplate. A "supernatant" is the liquid medium which has been removed from the cells. A buffer for assaying u-PA activity is added. The microplate is incubated for an appropriate amount of time, and the reactions are stopped with a termination buffer. Absorbance of the colorimetric product is measured.

Preferably, when determining whether a compound of interest is an agonist, the compound is administered to stably transfected cells and level of u-PA activity is measured or estimated and compared to the level of u-PA activity in stably transfected cells which have not come in contact with the compound of interest.

When determining whether a compound of interest is an antagonist, both the compound of interest and a known agonist should be administered to the stably transfected cells. The agonist and potential antagonist can be administered in any order (ie., agonist first and then potential antagonist or potential antagonist first and then agonist), as well as concurrently. After contacting the cells with both an agonist and the compound of interest, the level of u-PA activity in the stably transfected cells is measured or estimated and compared to the level of u-PA activity in stably transfected cells which have been contacted with the agonist alone.

Having generally described the invention, the same will be more readily understood by reference to the following examples, which are provided by way of illustration only, and are not intended to be limiting of the present invention.

EXAMPLE 1

Plasmid Transfection and Isolation of Clones

The cloned porcine kidney-derived cell line, LLC-PK1 (Bringhurst, F. R., et al., *Endocrinology* 132:2090–2098

(1993)) and subclones isolated after stable transfection with human PTH/PTHrp receptor cDNA were maintained in DMEM supplemented with 7% FBS and 1% penicillin/streptomycin with or without 1000 ug/ml G418 (all from GIBCO-BRL, Grand Island, N.Y.) under 5% $CO_2$ in air. To prepare cell lines stably expressing the human PTH/PTHrP receptor, confluent monolayers of cells were transfected with a full-length human PTH/PTHrP receptor cDNA constructed in the mammalian expression vector pcDNAIneo (Invitrogen, San Diego, Calif.) (Schipani, E., et al., *Science* 268:98–100 (1995)). In some cases, cells were co-transfected with the receptor cDNA and a plasmid encoding a dominant-negative PKA regulatory subunit mutant, "REV AB" (Clegg, C. H., et al., *J Biol Chem* 262:13111–13119 (1987)). Transfections were performed using the calcium-phosphate precipitation technique as previously described (Bringhurst, F. R., et al., *Endocrinology* 132:2090–2098 (1993)).

Eleven clonal cell lines were selected from among a total of over 100 independent subclones to provide a broad range of receptor expression (Table 1).

Table 1. Human PTH/PTHrP Receptor Expression and Signaling in Clonal LLC-PK1 Cells Subclones of LLC-PK1 cells stably transfected with hPTHR cDNA were analyzed by competitive radioligand (Scatchard) binding analysis and for maximal signaling responses (mean±SD of fold- or percent of basal)) to hPTH (1-34) (1000 nM). All values were obtained from at least two or three experiments performed in triplicate. Cyclic AMP accumulation and $IP_3$ formation in controls ranged from 3 to 10 pmol/well and from 1,000 to 1,500 cpm/well, respectively.

TABLE 1

| Subclone | Receptor Number/Cell ($\times 10^3$) | Apparent Kd (nM) | cAMP Accumulation | $IP_3$ Formation (% of Basal) |
|---|---|---|---|---|
| Human Receptor | | | | |
| HKRK B64 | 90 | 1.3 | 13 ± 2 | 116 ± 18 |
| HKRK C53 | 120 | 1.2 | 58 ± 16 | 112 ± 4 |
| HKRK B28 | 280 | 1.8 | 103 ± 17 | 107 ± 1 |
| HKRK C101 | 330 | 1.6 | 94 ± 1 | 114 ± 11 |
| HKRK C27 | 340 | 2.2 | 64 ± 8 | 113 ± 10 |
| HKRK C30 | 600 | 2.8 | — | 192 ± 44 |
| HKRK B5 | 840 | 3.9 | — | 462 ± 47 |
| HKRK B57 | 900 | 5.6 | — | 243 ± 31 |
| HKRK B7 | 950 | 4.5 | 99 ± 10 | 298 ± 21 |
| HKRK B54 | 1020 | 6.4 | — | 287 ± 19 |
| HKRH C58 | 1030 | 3.6 | — | 642 ± 106 |
| Rat Receptor | | | | |
| EW29 | 190 | 2.5 | 148 ± 16 | 289 ± 16 |
| EW5 | 320 | 2.3 | 130 ± 6 | 480 ± 14 |

EXAMPLE 2

Radioligand Binding

Specific binding to the PTH/PTHrp receptor was measured as previously described (Bringhurst, F. R., et al., *Endocrinology* 132:2090–2098 (1993)), with some modification. In brief, the cells were seeded into 24-well plates at a density of 2.5×10⁵ cells/well and cultured for a further 2 days before study. Cell layers were rinsed with ice-cold Buffer A [50 mM Tris-HCl (pH 7.7), 100 mM NaCl, 2 mM $CaCl_2$, 5 mM KCl, 0.5% FBS, and 5% heat-inactivated horse serum] and then incubated with $^{125}$I-labeled [$Nle^{8,18}$, $Tyr^{34}$]bovine (b) PTH(1-34) (1×10⁵ cpm/well), with or without unlabeled peptide, in 0.5 ml of Buffer A for 6 h in the cold room (2–8° C.). The binding reaction was terminated by aspirating the incubation mixture, after which the cells were washed twice with 0.5 ml of ice-cold Buffer A. After solubilizing the cells with 0.5 ml of Lysis Buffer (0.5 N NaOH+0.1% Triton X-100), measurements of radioactivity and protein were performed to calculate the receptor number per cell by Scatchard analysis, as previously described (Bringhurst, F. R., et al., *Endocrinology* 132:2090–2098 (1993)). All reagents, unless otherwise specified, were obtained from Sigma (St. Louis, Mo.), and all isotopes were purchased from Dupont-New England Nuclear (Boston, Mass.). The [$Nle^{8,18}$, $Tyr^{34}$]bPTH(1-34) was radioiodinated by the chloramine-T method and purified as previously described (Bringhurst, F. R., et al., *Endocrinology* 132:2090–2098 (1993)).

Radioligand competition assays and Scatchard analyses for two representative cell lines, HKRK B7 and HKRK B28, which express 950,000 and 280,000 hPTHRs per cell, respectively, are shown in FIGS. 1A–1D. Scatchard analysis of the all of the selected cell lines demonstrated a range of PTHR expression from 90,000 to 1,000,000 sites per cell, with apparent $K_d$'s between 1 and 7 nM (Table 1). In each case, the Scatchard analysis was linear, consistent with a single class of high affinity binding sites. The subsequent example described below was conducted with two cell lines, which were chosen as representative of those expressing relatively high (HKRK B7) and low (HKRK B28) densities of hPTHRs, respectively.

EXAMPLE 3

Human PHTR Signaling in LLC-PK1 Cells

Methods

Peptides and Other Reagents

All reagents, unless otherwise specified, were obtained from Sigma (St. Louis, Mo.), and all isotopes were purchased from Dupont-New England Nuclear (Boston, Mass.). [$Nle^{8,18}$, $Tyr^{34}$]bPTH(1-34), [$Tyr^{34}$]hPTH(1-34), hPTH(1-31), hPTH(3-34), hPTH(7-34), and hPTHrp(1-36) were synthesized with carboxy-terminal amide groups. The [$Nle^{8,18}$, $Tyr^{34}$]bPTH(1-34) was radioiodinated by the chloramine-T method and purified as previously described (Bringhurst, F. R., et al., *Endocrinology* 132:2090–2098 (1993)).

Cellular cAMP Accumulation

Cells were seeded into 24-well plates at a density of 2.5×10⁵ cells/well and cultured for a further 2 days before study. The cells were rinsed once with 0.5 ml of ice-cold Buffer B [10 mM HEPES (pH 7.4), 130 mM NaCl, 5 mM KCl, 1.2 mM $CaCl_2$, 1 mM $MgCl_2$, 1.2 mM $Na_2HPO^4$ 5 mM glucose, and 0.1% heat-inactivated BSA] supplemented with 1 mM isobtylmethylxanthine (IBMX), and placed on ice. Treatments were added to each well in 0.25 ml of IBMX-supplemented Buffer B, after which the plates were incubated at 37° C. for 15 min. The buffer then was rapidly aspirated, the plates were rapidly transferred onto liquid nitrogen, and the frozen monolayers were subsequently thawed directly into 0.5 ml of 50 mM HCl. The extracted cAMP then was measured using a commercial RIA kit (Dupont-New England Nuclear, Boston, Mass.). Results were expressed as fold-basal, where basal levels ranged between 38 and 128 pmol/mg protein/15 min. The basal level of cAMP accumulation in native LLC-PK1 cells was not consistently altered in subclones that expressed wild type PTH/PTHrp receptors.

Inositol 1,4,5-triphosphate ($IP_3$) Production

Cells were seeded into 24-well plates at a density of 2.5×10⁵ cells/well and cultured for a further 2 days before study. The cells were labeled at 37° C. for 16 h before assay with 3 uCi/ml of [$^3$H]myo-inositol in assay medium (serum- and inositol-free DMEM (GIBCO-BRL, Grand Island, N.Y.) supplemented with 0.1% BSA). After washing the cells with prewarmed assay medium containing 30 mM LiCl, they were incubated with 0.25 ml of assay medium containing 30 mM LiCl and stimulators (or vehicle) at 37° C. for various intervals(1–30 min). IP$_3$ formation was arrested by aspiration and immediate addition of 0.5 ml of ice-cold 5% TCA. The acid extracts then were extracted twice with two volumes of water-saturated ether and adjusted to pH 7.4 with concentrated NaOH and Tris base (final concentration=10 mM) prior to chromatography on AG 1×8 anion-exchange columns (Bio-Rad, Richmond, Calif.), as previously described (Guo, J., et al., *Endocrinology* 136:3884–3891 (1995)). After eluting other fractions (free [$^3$H]myo-inositol, glycerophosphate inositol, IP$_1$, and IP$_2$), IP$_3$ fractions were collected and their content of radioactivity was determined by liquid scintillation spectrometry (Beckman, model LS 6000IC).

Measurement of Cytosolic Free Calcium

Cytosolic free calcium was measured by dual fluorescence in cells loaded with the Ca$^{2+}$-sensitive intracellular probe fura-2. Cells were seeded onto glass coverslips at a density of 40,000–600,000/cm$^2$ and incubated for 2 days as described above. Coverslips were washed twice with PBS before loading in phosphate-free Buffer B containing 4 uM of fura-2/AM (Molecular Probes, Eugene, Oreg.) for 30 min at room temperature (22° C.). After washing twice with fura-free Buffer B, the coverslips were mounted in a cuvette containing 2 ml of phosphate-free Buffer B at 37° C. and the emission at 510 nm in response to alternating excitation at 340 and 380 nm was monitored using a ratiometric PTI Deltascan fluorescence spectrometer with excitation and emission bandwidths of 2 nm. After achieving a stable baseline, agonists were introduced by exchange into 2 ml of fresh buffer to which 10–20 ul of concentrated agonist stock (or vehicle alone) had been added. Peptide stocks were prepared in 0.1% trifluoroacetic acid, ionomycin and phorbol esters were dissolved in dimethyl sulfoxide and all other additives were prepared in water. Maximum and minimum fluorescence signals were obtained by exposure to modified buffers containing 1 uM ionomycin plus 20 mM calcium or 2 mM EGTA in the nominal absence of calcium, respectively, and autofluorescence was estimated from signals obtained in the presence of ionomycin plus 2.5 mM MnCl$_2$. Cytosolic free calcium then was determined as previously described (Bringhurst, F. R., et al., *Endocrinology* 132:2090–2098 (1993)).

Urokinase-type Plasminogen Activator (u-PA)

Cells were seeded into 96-well plates at a density of 6×10$^4$ cells/well and used the following day. The cells were washed once with 0.2 ml and then refed with 0.1 ml of prewarmed DMEM containing 0.05% BSA. After adding each stimulator, plates were returned to the incubator at 37° C. for 16 h. Conditioned medium (5 ul) then was transferred from each well to a clean microplate. Reactions were initiated by addition of 50 ul of u-PA assay buffer [90 mM Tris-HCl (pH 8.8), 0.45% Triton X-100, 14 ug/ml human plasminogen (Calbiochem, San Diego, Calif.) and 0.4 mg/ml S-2251 plasmin substrate (D-Val-Leu-L-Lys-NH-Np) (Sigma, St. Louis, Mo.)]. Plates were incubated first at 37° C. for 15 min and then at room temperature (22° C.) for 30 min. The reactions were terminated by addition of 10 ul of ice-cold 25% acetic acid. Absorbance of calorimetric product was measured at 405 nm within 1 hour. Activity was expressed in Ploug units/well, using purified human urokinase (Calbiochem) as a standard.

Cellular Phosphate Uptake

Cells were seeded into 24-well plates at a density of 2.5×10$^5$ cells/well and cultured for a further 2 days before study. Twenty four hours before assay, cells were refed with 0.5 ml of DMEM containing 0.1% BSA. The next day, cells were refed with serum-free medium (DMEM+0.1% BSA) containing drugs or peptides, and the incubations were continued at 37° C. under 5% CO$_2$ in air for another 6 hr. Cells then were washed with prewarmed Buffer B without BSA and Na$_2$HPO$_4$ and then were incubated at 37° C. for 5 min in 0.25 ml of the same buffer containing [$^{32}$P] orthophosphate (4 uCi/ml) and 0.1 mM Na$_2$HPO$_4$. Phosphate uptake was arrested by adding 1 ml of ice-cold sodium-free "stop buffer" [10 mM HEPES (pH 7.4), 140 mM choline chloride, and 5 mM sodium arsenate], followed by two further washes with same buffer. The drained cell layer then was solubilized in 0.5 ml of Lysis Buffer, and cell-associated radioactivity was determined by Cerenkov counting, as previously described (Guo, J., et al., *Endocrinology* 136:3884–3891 (1995)).

Results

The investigations of the properties of human PTHRs, stably expressed in LLC-PK1 cells, have produced two important observations. The first is the finding that the cell-surface density of the human PTHR is a key determinant, independent of ligand concentration, of the magnitudes of the individual signaling responses to PTH and that these changes occur over quite different, essentially non-overlapping, ranges of receptor density. In the course of these studies, hPTHR density-dependent differences in the temporal profile of the PLC response were also observed, and evidence of a role for PKA in sustaining the initial cytosolic calcium signal elicited by PTH in these cells was detected. The second major finding is that the putative signal-selective PTH analog hPTH(1-31) is not at all signal-selective in cells bearing human PTHRs, even though its PLC activating capacity is somewhat reduced in cells that express the rat PTHR. These results point to subtle differences in ligand-receptor interaction between human and other species of PTHRs and suggest that conclusions derived from rat models should be extrapolated with caution to human PTHR-expressing systems.

Influence of Cell-surface Density Upon Signaling Properties of Expressed hPTHRs

Figure 2A:
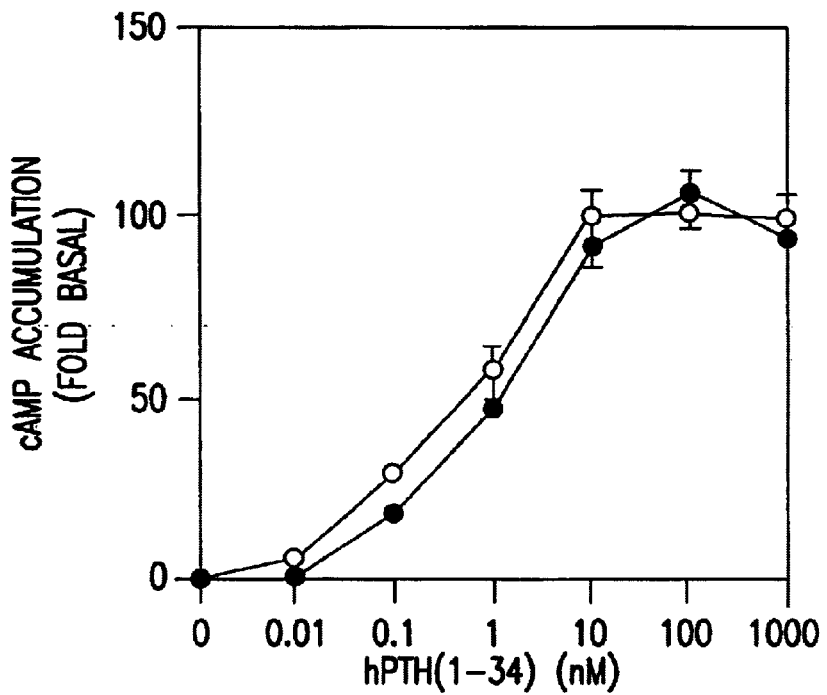
FIGS. 2A–2B. Stimulation of cAMP accumulation in LLC-PK1 cells expressing human PTH/PTHrP receptors. Cyclic AMP was measured in acid extracts of cells prepared after addition of the indicated peptides and incubation at 37° C. for 20 min.

Maximal PTH-dependent cAMP accumulation was assessed in the human PTHR-transfected LLC-PK1 subclones following incubation for 15 min with a high concentration (1000 nM) of hPTH(1-34) (Table 1). As reported previously for LLC-PK1 cells that stably expressed rat PTHRs (Guo, J., et al., *Endocrinology* 136:3884–3891 (1995)), the maximal adenylyl cyclase response was relatively independent of the surface density of human PTHRs above a relatively low threshold (relative to that required for PLC activation—see below). In the case of the human PTHR, however, this threshold for saturation of maximal AC activation appeared to lie between 120,000 and 280,000 (Table 1), which is at least 6 to 10-fold higher than that previously observed for the rat PTHR (Guo, J., et al., *Endocrinology* 136:3884–3891 (1995)). As expected, activation of AC by hPTH(1-34) in hPTHR-expressing LLC-PK1 cells was concentration-dependent and, as shown in FIG. 2A, the EC50's (approximately 1 nM) and maximal responses were identical in the cell lines HKRK B28 and HKRK B7.

Figure 3:
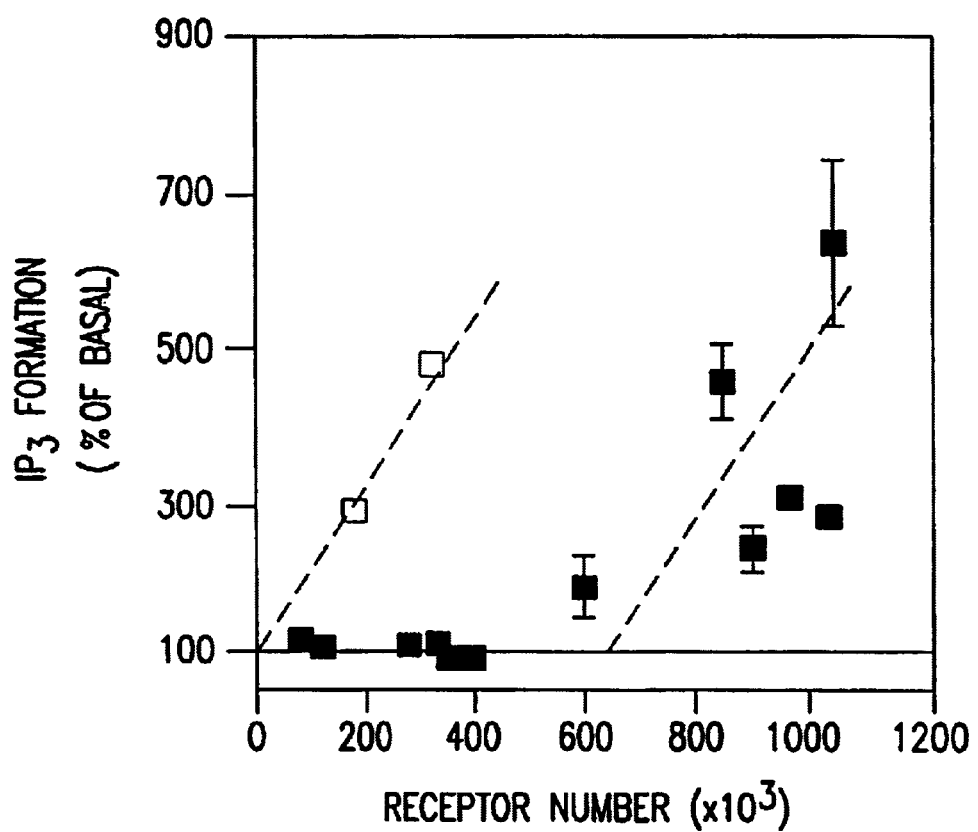
FIG. 3. Influence of PTH/PTHrP receptor density upon maximal activation of PLC by PTH in LLC-PK1 cells expressing human receptors. The maximal increase in IP$_3$ production, expressed as percentage of basal, is shown for LLC-PK1 cells expressing different densities of human (■) and rat (□) PTH/PTHrp receptors. Cells were stimulated for 30 min with hPTH(1-34) at a concentration of 1000 nM, which elicits maximal activation of this response (see FIG. 4B). Each point depicts the mean±SEM of three experiments performed in triplicate. The relation between PLC activity and receptor expression is shown schematically by the dashed lines for the rat (left) and human (right) receptors.

In previous studies involving expression of rat PTHRs in LLC-PK1 cells, maximal PLC activation by PTH, measured as total IP$_3$ released at 30 min, was found to be closely related to the density of rat PTHRs across a wide range of expression (i.e. from 20,000 to 400,000 receptors per cell) that clearly exceeded the threshold of receptor density required for saturation of maximal AC activation (Guo, J., et al., *Endocrinology* 136:3884–3891 (1995)). Similarly, as shown in FIG. 3 and Table 1, maximal PLC activation was strongly dependent upon PTHR density among LLC-PK1 subclones expressing human PTHRs. As in the case of AC activation, the relative efficiency with which the human PTHR coupled to PLC in these cells was approximately 3–5-fold less than that of the rat receptor.—i.e., roughly 3–5-fold more human than rat receptors were required for equivalent activation of PLC.

Figure 4A:
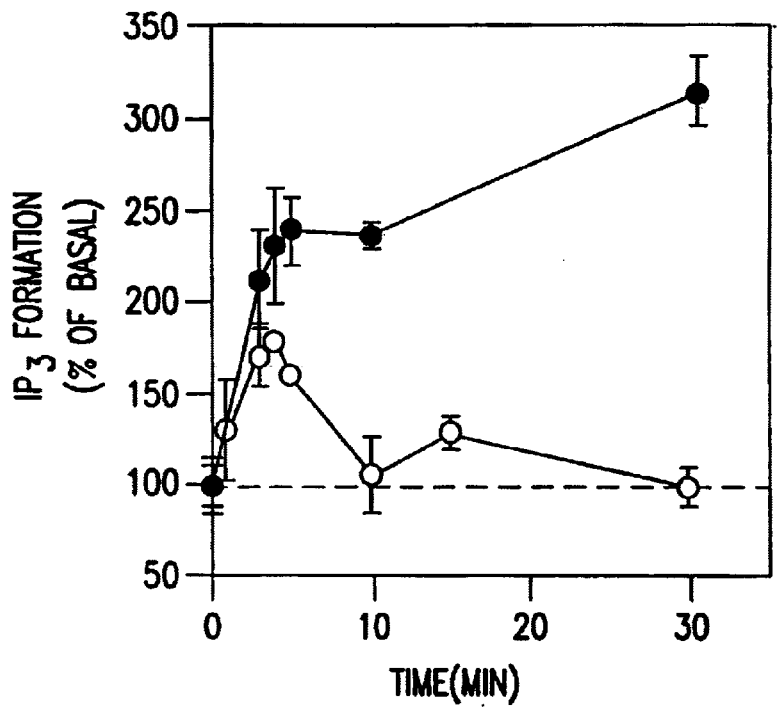
FIGS. 4A–4B. Comparison of time-and dose dependence of IP$_3$ production between HKRK B7 and HKRK B28 cells.

In several PTH-responsive cell lines that express lower numbers of PTHRs—i.e. UMR 106 cells (approximately 70,000 receptors per cell)—a pattern of very rapid but transient PLC activation has been described (Yamaguchi, D. T., et al., *J Biol Chem* 262:7711–7718 (1987)). Seeking to determine if such a transient pattern might underlie the absence of a sustained PLC activation in LLC-PK1 cells expressing fewer than 400,000 human PThRs, preliminary studies were performed that demonstrated increased $IP_3$ at an earlier time (4 min) in HKRK C53, HKRK B28 and HKRK C101 cells (120,000, 280,000 and 330,000 PTHRs per cell, respectively), though not in HKRK B64 cells (90,000 sites per cell) (data not shown). The time course of PLC activation then was studied in more detail in HKRK B28 cells and compared with that in HKRK B7 cells. As shown in FIG. 4A, transient PTH-stimulated $IP_3$ formation was observed in HKRK B28 cells within the first few minutes of PTH exposure. This response peaked at 4 min and was followed by a rapid decrease to basal levels by 10 min. In contrast, as previously reported for LLC-PK1 cells that expressed 300,000 rat PTHRs/cell (Guo, J., et al., *Endocrinology* 136:3884–3891 (1995)), $IP_3$ formation in HKRK B7 cells continued to increase between 10 and 30 minutes, although a more rapid initial phase also was evident in these cells.

Figure 4B:
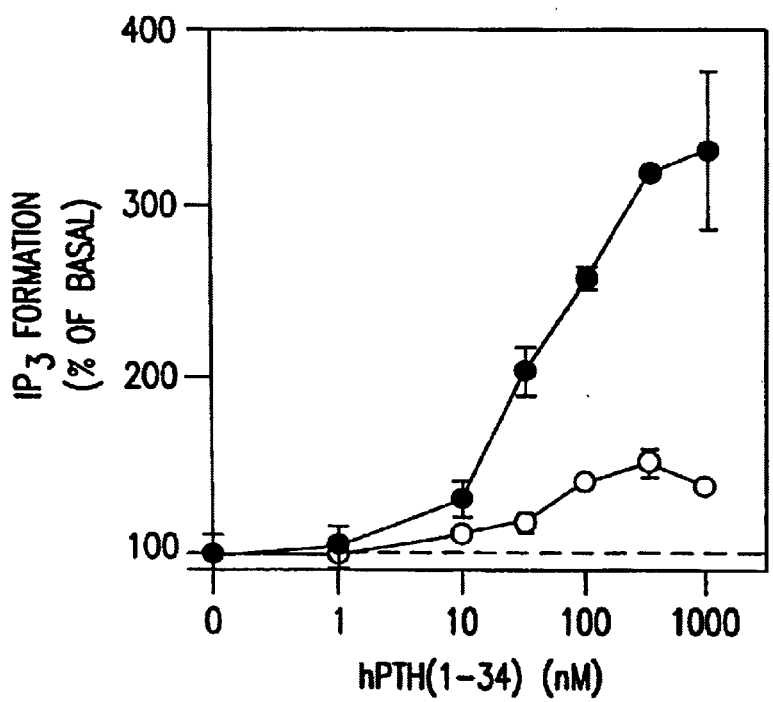

The different temporal patterns of PTH-induced PLC activation observed in HKRK B28 and HKRK B7 cells suggested several possibilities, including more extensive desensitization, which might more rapidly extinguish the weaker PLC response in HKRK B28 cells, or possibly recruitment, via higher receptor expression, of a more weakly coupled but distinct mechanism of $IP_3$ formation in the HKRK B7 cells. In an effort to distinguish these, it was assessed whether, as reported in other systems (Menniti, F., et al., *Mol Pharmacol* 40:727–733 (1991)), the concentration dependence might be different for the rapid (i.e. 4 min) vs. the sustained (i.e. 30 min) PLC responses in HKRK B28 and HKRK B7 cells, respectively. As shown in FIG. 4B, however, although the extent of the maximal responses at 4 min in HKRK B28 and at 30 min in HKRK B7 were very different, the $EC_{50}$'s of the two responses were identical (approximately 20–30 nM) and similar to that previously reported for the rat PTHR in these cells (Guo, J., et al., *Endocrinology* 136:3884–3891 (1995)). Moreover, as shown in Table 2, the ligand specificity of the two responses also was similar, in that PLC activation by hPTH(1-34) and hPTHrP(1-36) was equivalent within each cell line and neither hPTH(3-34) nor hPTH(7-34) exhibited any consistently detectable activity in either case. Overall, these results did not suggest important differences in ligand-receptor coupling or selectivity between the transient PLC response in HKRK B28 and the sustained response in HKRK B7.

Table 2. Activation of Phospholipase-C by PTH or PTHrP Peptides in HKRK B7 and HKRK B28 Cells.

HKRK B7 cells and HKRK B28 cells, previously loaded with [$^3$H]myo-inositol, were incubated with each peptide (1000 nM) for 30 min or 4 min, respectively. The formation of $IP_3$ is expressed as a percentage of the amount measured in vehicle-treated controls. Values shown are means±SEM of triplicate determinations.

TABLE 2

| Peptide (1000 nM) | HKRK B7 (30 min stimulation) | HKRK B28 (4 min stimulation) |
|---|---|---|
| control | 100 ± 5 | 100 ± 3 |
| hPTH (1–34) | 298 ± 24 | 172 ± 9 |
| hPTH (1–31) | 275 ± 21 | 170 ± 14 |
| hPTH (3–34) | 103 ± 1 | 85 ± 9 |
| hPTH (7–34) | 122 ± 7 | 92 ± 10 |
| hPTHrP (1–36) | 93 ± 6 | 160 ± 9 |

Among the expected consequences of PLC activation via the human PTHR in LLC-PK1 cells would be release of sequestered calcium from intracellular stores (Bringhurst, F. R., el al., *Endocrinology* 132:2090–2098 (1993), Dunlay, R., and Hruska, K., *Am J Physiol* 258:F223–231(1990), Yamaguchi, D. T., et al., *J Biol Chem* 262:7711–7718 (1987), Pines, M., et al., *Bone* 18:381–389 (1996)). Accordingly, cytosolic free calcium was measured in HKRK B28 and HKRK B7 cells following exposure to hPTH(1-34). As shown in FIG. 5, addition of hPTH(1-34) (100 nM) to monolayers of Fura 2AM-loaded cells caused a rapid elevation of cytosolic free calcium that peaked at 400–600 nM within 20 sec and slowly decayed thereafter. No significant difference in the magnitude or time-course of this response was observed between HKRK B7 and HKRK B28 (cf FIGS. 5A and 5C), despite the larger $IP_3$ response in the HKRK B7 cells (FIG. 4A).

Figure 5A:
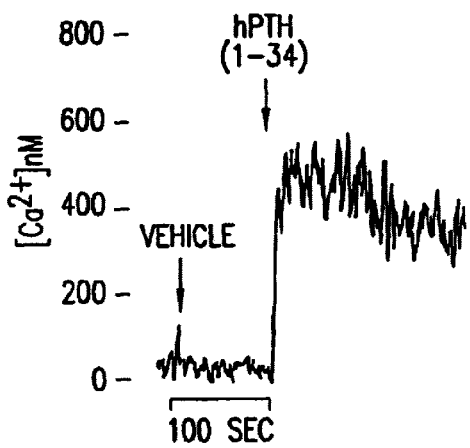
FIGS. 5A–5D. Cytosolic free calcium responses to hPTH in LLC-PK1 cells expressing human PTH/PTHrp receptors. Cytosolic free calcium was measured in fura 2AM-loaded confluent monolayers of cells. Responses were measured in HKRK B7 cells following addition of hPTH(1-34) (FIG. 5A) or hPTH(1-31) (FIG. 5B); in HKRK B28 cells following hPTH(1-34) (FIG. 5C); and in AB45 cells following hPTH(1-34) (FIG. 5D). Basal cytosolic free calcium concentrations and those following addition of sCT in these cell lines were virtually identical—i.e. 20–50 nM and 400–500 nM, respectively. These results shown are representative of at least 5 independent experiments with each cell line.
Figure 5B:
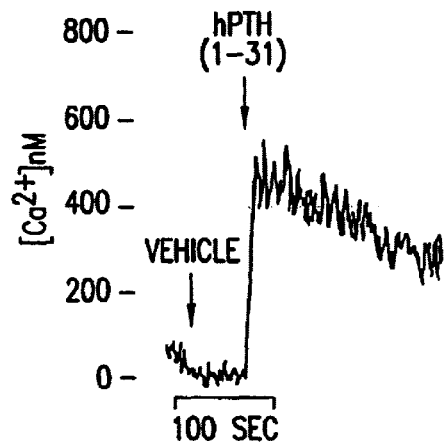
Figure 5C:
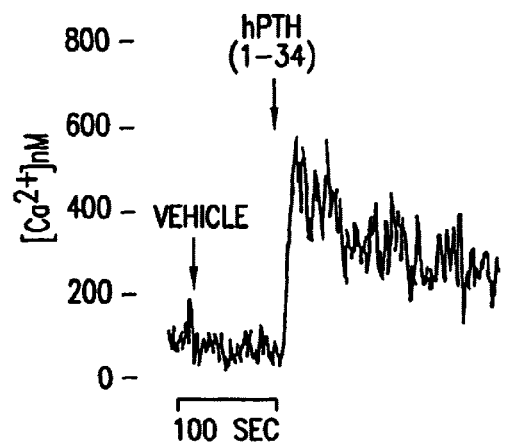
Figure 5D:
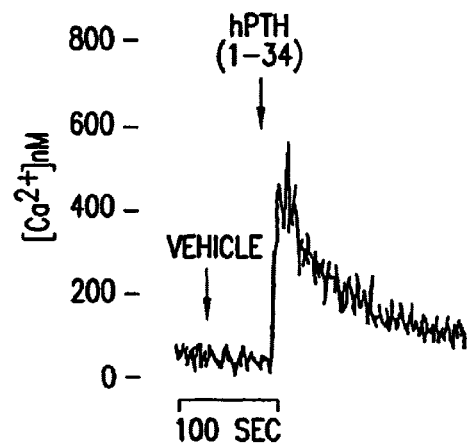

To examine the possibility that activation of the cAMP pathway might be responsible for the cytosolic free calcium response to PTH in these cells, AB45 cells were studied, in which human PTHRs (370,000/cell) were co-expressed with REV AB, a dominant-negative inhibitor of both basal and hormone-stimulated protein kinase A (PKA) (Clegg, C. H., et al., *J Biol Chem* 262:13111–13119 (1987), Fukayama, S., et al., *Endocrinology* 134:1851–1858 (1994)). As shown in FIG. 5D, a robust cytosolic calcium response to hPTH(1-34) still was observed in these cAMP-resistant cells and was of comparable magnitude to that observed in cAMP-responsive HKRK B28 cells that expressed a similar number of hPTHRs. Thus, the rapid increase in cytosolic free calcium triggered by activation of the hPTHR in these cells apparently is not mediated by cAMP. Interestingly, however, it was observed that the calcium transient decayed more rapidly in the cAMP-resistant AB45 cells than in HKRK B28 cells, approaching basal levels within only 2–3 min (FIG. 5D). This occurred despite the fact that the magnitude and temporal pattern of $IP_3$ formation in AB45 cells was nearly identical with that in HKRK B28 cells (data not shown). Neither 8BrcAMP (1 mM) nor the active phorbol ester TPA (100 nM) evoked a rapid calcium response (not shown). These results implied that the magnitude of the initial cytosolic free calcium response was most closely related to PLC activation, whereas the duration of the response may have been influenced predominantly by activation of the PKA pathway, possibly through enhanced entry of extracellular calcium (Yamaguchi, D. T., et al., *J Biol Chem* 262:7711–7718 (1987)).

Regulation of Biologic Responses by PTH

To determine if the changes in signaling efficiency and selectivity observed at different levels of human PTHR expression in LLC-PK 1 cells could result in alterations in integrated distal biologic responses to PTH, two well-characterized hormonal responses in these cells were studied—secretion of u-PA and sodium-dependent active transport of inorganic phosphate.

Figure 6A:
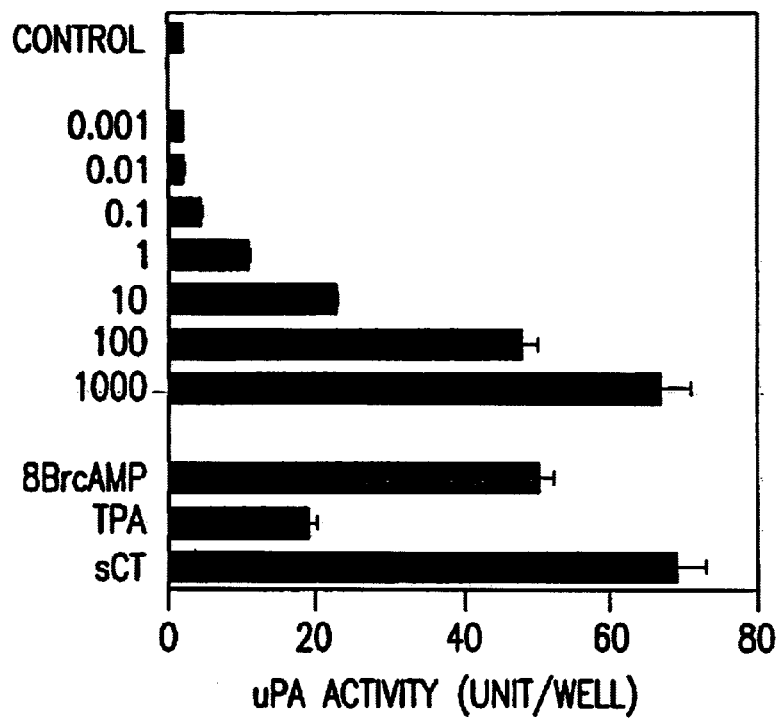
FIGS. 6A–6B. Stimulation of urokinase-type plasminogen activator (u-PA) secretion by LLC-PK1 cells. Urokinase-type plasminogen activator activity was measured in conditioned medium of (FIG. 6A) HKRK B7 cells or (FIG. 6B) HKRK B28 cells, 16 hr after addition of agonists as follows: HPTH(1-34) (concentration shown in nM), 8BrcAMP (1 mM), TPA (100 nM), or sCT (1000 nM). Results are expressed in Ploug units/well using purified human urokinase as a standard. Each bar depicts the mean±SEM of a representative experiment performed in triplicate. Similar results were obtained in over 10 individual experiments.
Figure 6B:
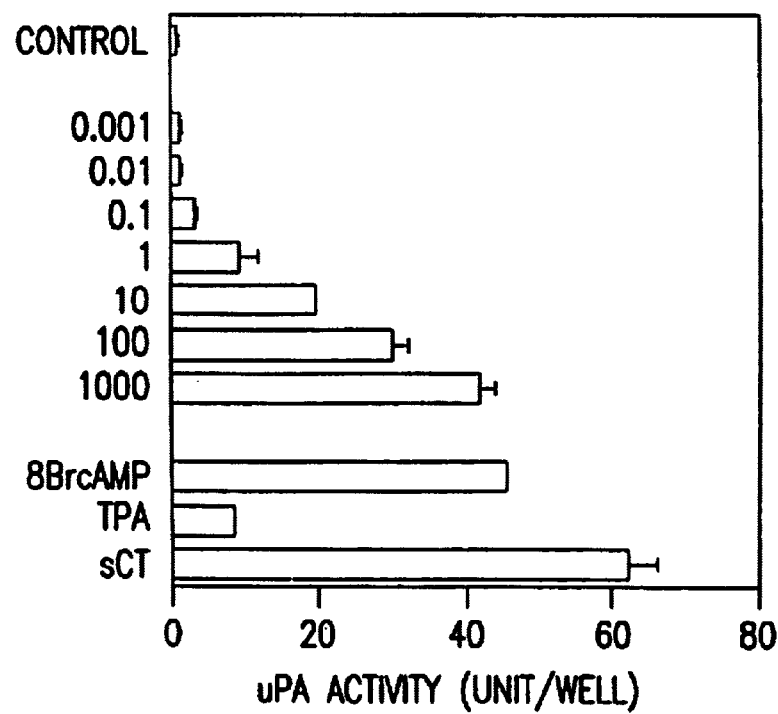

Secretion of urokinase-type plasminogen activator (u-PA) by LLC-PK1 cells previously had been reported in response to activation of both the PKA and PKC pathways by calcitonin (Jans, D. A., and Hemmings, B. A., *FEBS Lett* 205:127–131 (1986)). This assay was adapted to provide a convenient spectrophotometric bioassay to report activation of AC or PLC via the human PTHR in these cells. As shown in FIG. 6, incubation with hPTH(1-34) for 16 hr elicited a dose-dependent increase in u-PA secretion from both HKRK B7 and HKRK B28 cells. In both cell lines, 8BrcAMP and TPA, pharmacologic activators of PKA and PKC respectively, also strikingly induced this activity, reconfirming that both PKA and PKC pathways were linked to u-PA production. Maximal production of u-PA by HKRK B7 in response to hPTH(1-34) was greater than that in HKRK B28, both in absolute terms and in relation to other agonists such as calcitonin or 8BrcAMP (FIG. 6).

Figure 7:
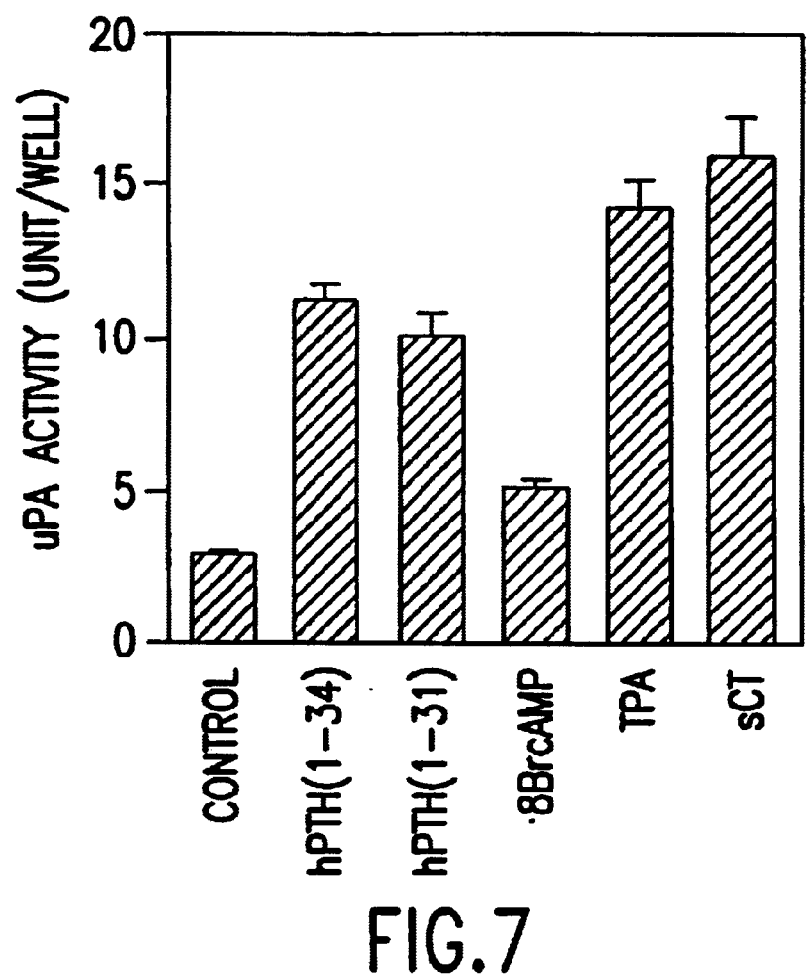
FIG. 7. Stimulation of u-PA activity in LLC-PK1 cells that express dominant-negative inhibition of protein kinase A. Secretion of u-PA was measured 16 hr after addition of agonist to AB45 cells, which co-express human PTHRs and REV AB, a dominant-negative inhibitor of PKA. Results are expressed in Ploug units/well, using purified human urokinase as a standard. Each point depicts the mean±SEM of a representative experiment performed in triplicate. Similar results were obtained from at least 5 individual experiments.

Because the sensitivities and magnitudes of the cAMP responses to PTH in these two cell lines were identical, it seemed possible that the greater maximal u-PA response to PTH observed in HKRK B7 versus HKRK B28 cells might reflect the sustained activation of PLC seen only in the HKRK B7 cells. Moreover, the $EC_{50}$ for stimulation of u-PA production by hPTH(1-34) (10–20 nM) was more similar to that for activation of $IP_3$ formation (20–30 nM) than for cAMP accumulation (1 nM), particularly in HKRK B7 cells. Also, the maximal u-PA response to PTH was higher than that of 8BrcAMP in HKRK B7 (but not in HKRK B28 cells), consistent with activation, by the more abundant hPTMs in these cells, of an additional, PKA-independent mechanism. Further evidence for involvement of a cAMP-independent (presumably PKC-dependent) mechanism of PTH-induced u-PA secretion in these cells was obtained using the cAMP-resistant AB45 cells (FIG. 7). As expected, the u-PA response to 8BrcAMP was nearly obliterated in these cells, whereas that to phorbol ester was well-maintained. The PTH response, like that to calcitonin, was dramatically attenuated but remained significantly greater than that achieved with a maximal concentration of 8BrcAMP. This result further supports a role for mechanisms independent of PKA in mediating PTH-stimulated u-PA secretion in these cells.

Figure 8:
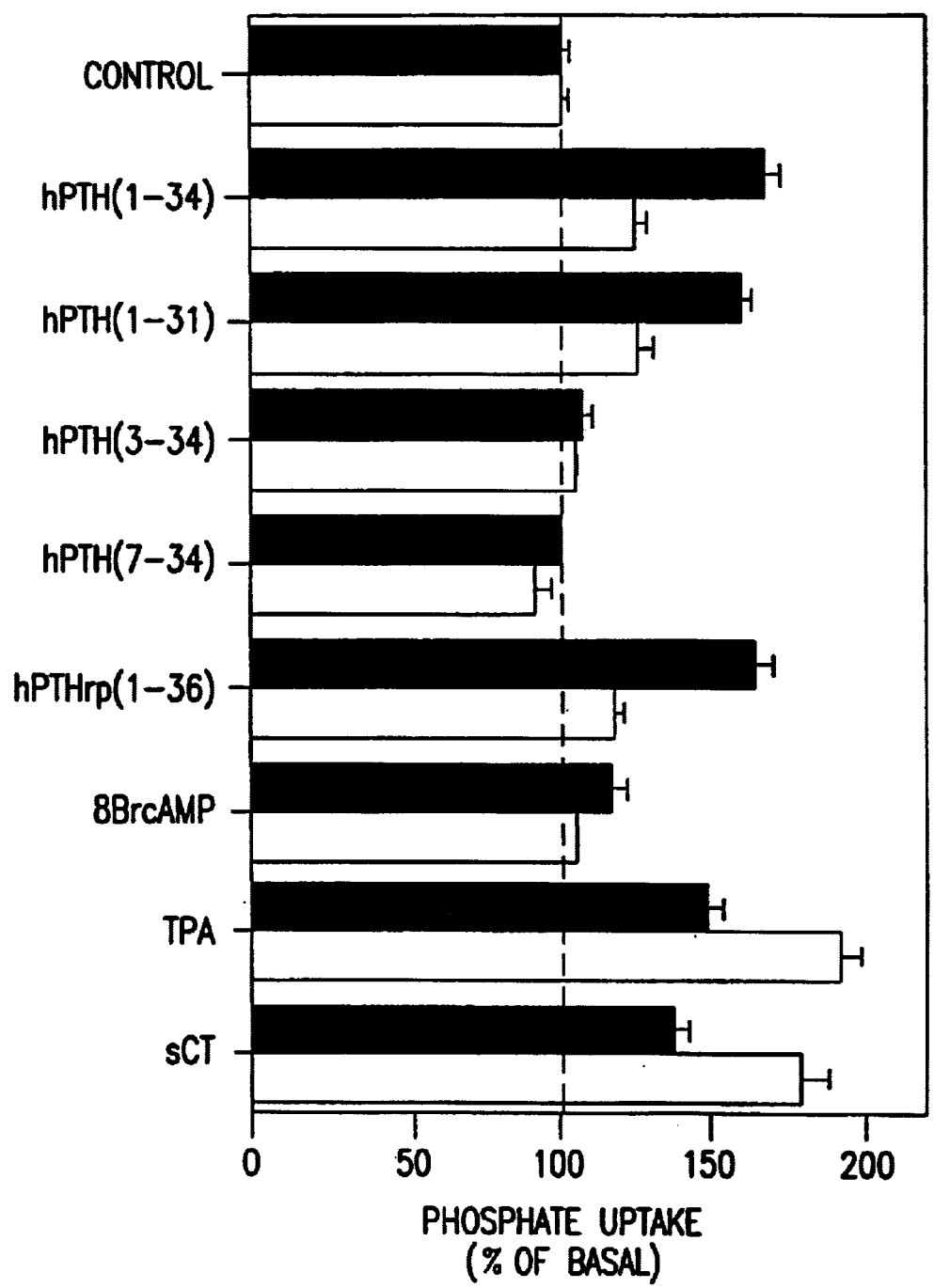
FIG. 8. Regulation of phosphate uptake by PTH in HKRK B7 and HKRK B28 cells. Phosphate uptake was measured in HKRK B7 cells (closed bars) and HKRK B28 cells (open bars) following incubation for 6 hr in serum-free medium containing vehicle, hPTH/PTHrp peptides (1000 nM), 8BrcAMP (1 mM), TPA (100 nM), or sCT (1000 nM). Preliminary experiments (not shown) demonstrated maximal responses to hPTH/PTHrp peptides at concentrations of 1000 nM or above. Results are expressed as percentage of basal, and each bar represents the mean±SEM of a representative experiment performed in triplicate. Similar results were obtained from at least 5 individual experiments.

It was previously reported that stimulation of sodium-dependent phosphate uptake following activation of the rat PTHR in LLC-PK1 cells was mediated principally by the PLC/PKC pathway (Guo, J., et al., *Endocrinology* 136:3884–3891 (1995)) Similar observations have been reported by others in CHO cells (Kaufmann, M., *Mol Cell Endocrinol* 104:21–27 (1994)). The regulation of this response by PTH in HKRK B7 and HKRK B28 cells that expressed the human PTHR was therefore examined. As shown in FIG. 8, phosphate uptake was stimulated significantly by hPTH(1-34) in these cells. This PKC-dependent action of PTH(1-34) was observed in both HKRK B28 and HKRK B7 cells, suggesting that the transient PLC response observed in the HKRK B28 cells was sufficient to induce this more sustained biologic response. This conclusion was further supported by the observation that phosphate uptake also was stimulated over 2-fold by PTH(1-34) in the cAMP-resistant AB45 cells (data not shown), in which, as noted above, the only measurable PTHR signal was the transient stimulation of PLC and associated increase in cytosolic free calcium.

Effects of changes in PTHR density upon ligand-dependent activation of the AC and PLC effectors were observed that, although obtained using a nonhomologous model system in vitro, could have important physiologic implications. Differences in specific patterns and relative intensities of the intracellular second messenger signals generated by PTHR activation, particularly in osteoblasts or marrow stromal cells, may be critical in transmitting to both the immediate target cell and neighboring cells of the osteoclastic lineage information about various temporal patterns and concentration profiles of circulating PTH that ultimately may have profoundly different effects on bone (Dempster, D. W., et al., *Endocrine Rev* 14:690–709 (1993)). Accordingly, insights into possible mechanisms of such differential signaling may be crucial for understanding the distinct mechanisms that must underlie the anabolic and catabolic effects of PTH on bone in vivo. The influence of receptor expression on the "signaling phenotype" of the PTHR also could be important in modulating responses of chondrocytes to high local concentrations of PTHrP in developing bone (Lanske, B., et al., *Science* 273:663–666 (1996), Lee, K., et al., *Endocrinology* 137:5109–5118 (1996))

One mechanism for such differential signaling, based simply upon changes in the extracellular ligand concentration, is evident from previous studies in which substantial differences in ligand sensitivity ($EC_{50}$) of the AC and PLC responses to PTH have been observed upon initial exposure of naive cells to PTH (Schneider, H., *Eur J Pharmacol* 246:149–155 (1993), Pines, M., et al., *Endocrinology* 135:1713–1716 (1994), Guo, J., et al., *Endocrinology* 136:3884–3891 (1995), Pines, M., et al., *Bone* 18:381–389 (1996), Kaufmann, M., *Mol Cell Endocrinol* 104:21–27 (1994)). The present inventors report similarly striking differences in sensitivity of the AC and PLC responses to PTH in LLC-PK1 cells that express hPTHRs—i.e. the $EC_{50}$ that was observed for activation of AC was 10–100-fold lower than that for PLC stimulation.

Another mechanism of differential signaling could involve disproportionate desensitization of PTHR coupling to different G proteins following prior exposure to ligand. Desensitization of PTHR signaling has been widely described (Mitchell, J., and Goltzman, D., *Endocrinology* 126:2650–2660 (1990), Abou-Samra, A. B., et al., *Endocrinology* 135:2588–2594 (1994), Fukayama, S., et al., *Endocrinology* 134:1851–1858 (1994), Yamamoto, I., et al., *Endocrinology* 122:1208–1217 (1988), Freyaldenhoven, A. M., et al., *Am J Physiol* 262:E87–E95 (1992)), and differences noted among the various transduction pathways with respect to the temporal patterns and magnitudes of these desensitization events also could modulate the relative intensity of subsequent signaling along each route.

A third mechanism for generating differential signaling was suggested by the previous finding that the relative magnitudes of the maximal AC and PLC signals were strikingly different, depending upon the number of rat PTHRs expressed on the cell surface (Guo, J., et al., *Endocrinology* 136:3884–3891 (1995)). Thus, for any given extracellular ligand concentration, variations in the number of cell-surface rPTHRs influenced not only the magnitude of a given intracellular signal, but also its intensity relative to that of other signals, thereby altering the pattern of intracellular signal transduction independently of changes in ligand concentration. The present studies indicate that this differential influence of receptor expression on AC versus PLC signaling efficiency may apply to human PTHRs as well and may occur without any change in the $EC_{50}$'s of the individual responses. Analogous results recently were reported for comparisons of AC and cytosolic free calcium signaling in HEK-293 human kidney cells that expressed different numbers of human PTHRs (Pines, M., et al., *Bone* 18:381–389 (1996)). This dissociation of changes in ligand sensitivity from changes in efficiency of G protein and/or effector coupling suggests that the structural determinants of the PTHR involved in agonist recognition and activation may operate relatively independently of those involved in G protein/effector interaction. The physiologic relevance of these observations is supported by the substantial changes in expression of the PTHR known to occur in cells of bone or during repeated PTH exposure in vitro or in vivo (Mitchell, J., and Goltzman, D., *Endocrinology* 126:2650–2660 (1990), Abou-Samra, A. B., et al., *Endocrinology* 135:2588–2594 (1994), Fukayama, S., et al., *Endocrinology* 134:1851–1858 (1994), Yamamoto, I., et al., *Endocrinology* 122:1208–1217 (1988); Freyaldenhoven, A M., et al., *Am J Physiol* 262:E87–E95 (1992); Forte, L., et al., *Am J Physiol* 242:E 154–E163 (1982); Bellorin, F. E., et al., *Kidney Int* 47:38–44 (1995)). Moreover, variation of endogenous PTHR expression within the range that was studied in LLC-PK1 cells has been described in other cell systems in which endogenous PTHR genes are expressed (Yamamoto, I., et al., *Endocrinology* 122:1208–1217 (1988), Shukunami, C., et al., *J Cell Biol* 133:457–468 (1996)).

Several additional aspects of the signaling properties of hPTHRs that were have observed here are worthy of comment. First, it is of interest that the efficiencies with which the human PTHR couples to the AC and PLC responses in LLC-PK1 cells were substantially and coordinately reduced when compared with those for the corresponding responses in cells expressing rat PTHRs. This is very evident in FIG. 3, for example, where roughly 3–5-fold more human than rat PTHRs were required to achieve comparable maximal activation of PLC. An analogous difference in efficiency of AC coupling is suggested by comparing the data for the hPTHR in Table 1 with results that were previously reported for rat PTHRs in these cells (Guo, J., et al., *Endocrinology* 136:3884–3891 (1995)). This "rightward shift" of the relation between overall signaling efficiency and receptor density may reflect an intrinsic property of the human PTHR or, alternatively, a relative species incompatibility between the human receptor and the intracellular signal transducers expressed by the porcine cells used here. More efficient coupling of transfected human PTHRs to PLC or cytosolic calcium signaling has been observed in cells of primate or human origin (Pines, M., et al., *Bone* 18:381–389(1996), Schipani, E., et al., *Science* 268:98–100 (1995)). Direct comparisons of the functions of transfected rat and human PTHRs in cells derived from a wider range of species will be needed to clarify this issue.

Second, it was found that not only the magnitude but also the temporal profile of the $IP_3$ response (at maximal concentrations of ligand) was related to receptor density. Specifically, the PLC response at lower levels of PTHR expression was transient, lasting less than 10 min, whereas that triggered at higher PTHR densities was considerably more sustained. The explanation for this difference is not immediately clear. The mechanism(s) of the rapid decline from the peak of measured $IP_3$ that was observed in the HKRK B28 cells, which is typical of many receptor responses (Berridge, M., and Irvine, R., *Nature* 341:197–205 (1989)), probably is complex and could include (a) termination of the initial stimulus (via receptor desensitization or internalization), (b) depletion of a limited pool of membrane phosphatidylinositol 4,5-bisphosphate substrate accessible to the PTHR (especially in the presence of lithium (Nahorski, S. R., et al., *Trends Pharmacol Sci* 12:297–303 (1991))), or (c) rapid induction of enzymes that metabolize inositol polyphosphates—notably the inositol 1,4,5-trisphosphate 5-phosphatase—which may be mediated in part by activation of PKC (Nahorski, S. R, et al., *Trends Pharmacol Sci* 12:297–303 (1991), Shears, S. B., *Biochem J* 260:313–324 (1989)). Substrate depletion seems an unlikely explanation in the system, as the peak rate of substrate hydrolysis and $IP_3$ formation at 4 min actually was greater in the HKRK B7 cells with the more prolonged response. It is not yet known, however, if the distribution of expressed PTHRs is uniform throughout the membranes of these polarized epithelial cells at all levels of hPTHR expression that were studied. It is possible, for example, that PTHR distribution might be more restricted at lower rates of receptor synthesis, which could limit the size of the substrate pool available to the receptor in such cells and permit "local" substrate depletion. It was considered that the more prolonged PLC response in HKRK B7 cells could be due simply to a more intense and protracted activation of the enzyme, sustained by a much larger number of occupied receptors held in an active configuration in these cells, that was sufficient to nearly saturate the phosphatases involved in metabolizing $IP_3$ (Shears, S. B., *Biochem J* 260:313–324 (1989)). The results seem most consistent with this possibility, as no difference could be detected in $EC_{50}$'s of the responses measured at 4 min vs. 30 min, nor was an obvious difference detected in ligand selectivity that might have pointed to two different mechanisms. In contrast to these differences in the PLC responses, activation of AC by PTH appeared to proceed identically over the first 15 min in both cell lines. Moreover, in experiments not shown, it was also verified, by direct measurement of enzyme activity at intervals up to 24 hr after addition of 1000 nM hPTH(1-34), that this is true of the more sustained PKA responses in these cells as well.

A third interesting feature of hPTHR signaling in these cells concerns the cytosolic calcium responses that were observed. Given the differences discussed above in PLC activation profiles between HKRK B28 and HKRK B7 cells, the widely accepted view that $IP_3$ is a major determinant of calcium release from intracellular stores during activation of G protein-coupled receptors (Berridge, M. J., *Nature* 361:315–325 (1993)), and the recent demonstration, in permeabilized HEK-293 cells expressing human PTHRs, that PTH and $IP_3$ appear to compete for release from the same intracellular pool of calcium (Pines, M., et al., *Bone* 18:381–389 (1996)), it is perhaps surprising that the cytosolic free calcium transients triggered by PTH in these two cell lines were virtually identical, both in time and magnitude. The results with cAMP-resistant AB45 cells did suggest that the sustained phase of cytosolic free calcium elevation may be related to activation of PKA—possibly by promoting entry of extracellular calcium (Yamaguchi, D. T., et al., *J Biol Chem* 262:7711–7718 (1987))—but the initial phase of the calcium response appeared to be independent of PKA. Further, other experiments, in which forskolin, 8-bromo-cAMP and phorbol ester also failed to elicit calcium responses, offered no evidence for direct involvement of PKA or PKC in eliciting this response. It was concluded that the rapid cytosolic calcium response to PTH is most closely related to the initial increase in $IP_3$ in these cells and, further, that the amount of $IP_3$ generated acutely in HKRK B28 cells, although less than that produced in HKRK B7 cells, must be sufficient to achieve maximal release of calcium from the $IP_3$-sensitive intracellular pool.

Signaling and Biological Activity of hPTH Analogs

Several PTH analogs were reported to exhibit signal-selectivity in PTH-responsive cells of non-human origin. These include PTH(3-34) and PTH(7-34), which have been shown in some systems to selectively activate PKC and/or cytosolic calcium transients (Fujimori, A., et al., *Endocrinology* 128:3032–3039 (1991), Abou-Samra, A. B., et al., *Endocrinology* 135:2588–2594 (1994); Azarani, A., et al., *J Biol Chem* 271:14931–14936 (1996); Chakravarthy, B. R, et al., *Biochem Biophys Res Commun* 171:1105–1110 (1990); Fujimori, A., et al., *Endocrinology* 130:29–36 (1992); Jouishomme, H., et al., *Endocrinology* 130:53–60 (1992); Janulis, M., et al., *Endocrinology* 133:713–719 (1993)), and PTH(1-31), which has been reported to activate AC but not PKC in rat osteosarcoma cells and primary rat spleen cells (Rixon, R. H., et al., *J Bone Miner Res* 9:1179–1189 (1994), Whitfield, J. F., and Morley, P., *Trends Pharmacol Sci* 16:382–386 (1995), Jouishomme, H., et al., *Endocrinology* 130:53–60 (1992)). Because such fragments have been considered as candidates for clinical use (Dempster, D. W., et al., *Endocrine Rev* 14:690–709 (1993), Whitfield, J. F., and Morley, P., *Trends Pharmacol Sci* 16:382–386 (1995)) it was determined if these analogs would display the expected signal-selectivity via human PTHRs.

Figure 2B:
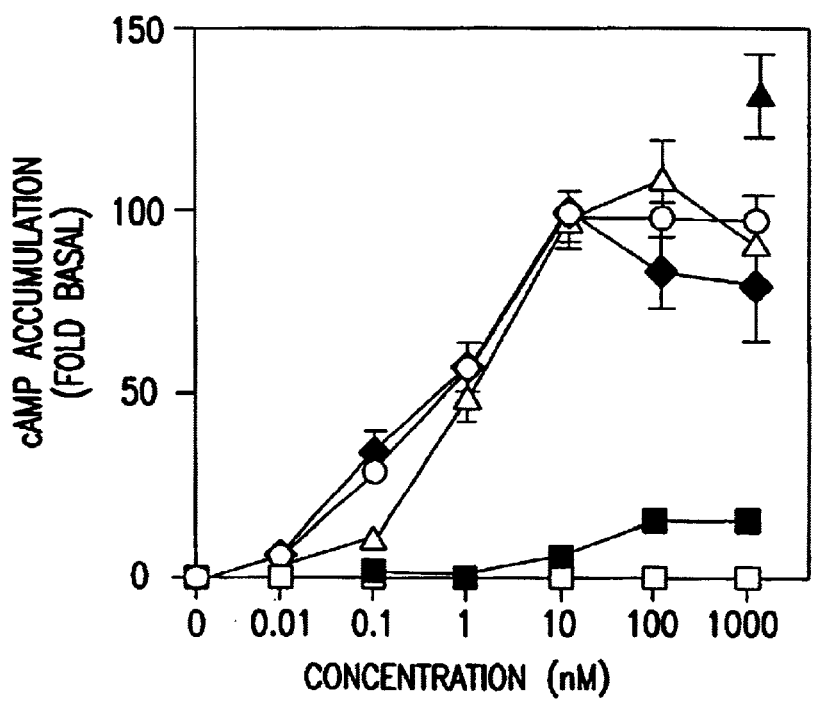

As shown in FIG. 2B, activation of AC in HKRK B28 cells was stimulated significantly by hPTH(3-34) at concentrations of 10 nM and above, although the response to 1000 nM of this peptide was only 16% of the maximal response to hPTH(1-34). Human PTH(7-34) failed to activate AC at all concentrations tested, whereas the responses to hPTHrP (1-36) and hPTH(1-31) were indistinguishable from that to hPTH(1-34). Similar results were obtained in experiments with HKRK B7 cells (data not shown).

When tested at concentrations of 1000 nM, neither hPTH (3-34) nor hPTH(7-34) activated PLC significantly, even in HKRK B7 cells that expressed nearly 1 million receptors per cell (Table 2). In contrast, both hPTHrP (1-36) and, unexpectedly, hPTH(1-31) stimulated PLC equivalently to hPTH(1-34) in both HKRK B28 (at 4 min) and HKRK B7 (at 30 min). Human PTH(1-31) (100 nM) also fully activated cytosolic free calcium transients in HKRK B7 cells (FIG. 5B), whereas neither hPTH(3-34) nor hPTH(7-34) (100 nM) induced this response (not shown).

Figure 9:
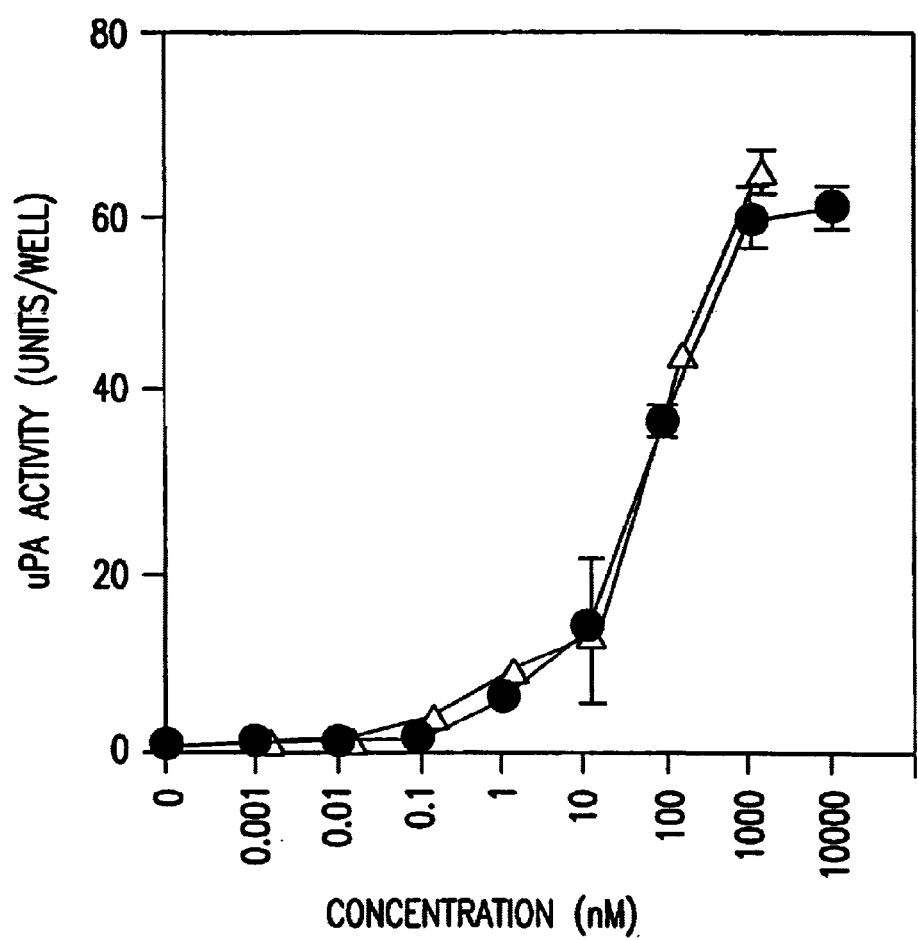
FIG. 9. Stimulation of u-PA secretion by hPTH(1-31) and hPTH(1-34) in HKRK B7 cells. Urokinase-type PA activity was measured 16 hr after addition of hPTH(1-34) (●) or hPTH(1-31) (Δ) at the indicated concentrations and expressed as Ploug units/well using purified human urokinase as a standard. Each point is the mean±SEM of a representative experiment performed in triplicate. Similar results were obtained in at least 6 individual experiments.

In the u-PA bioassay, which is mainly dependent upon PKA activation but also reflects PKA-independent signaling (as described above), the activities of hPTH(3-34), hPTH (7-34) and hPTH(1-31) were concordant with their signaling properties. Thus, hPTH(3-34) was partially active (50–60% of maximal response to hPTH(1-34)), whereas hPTH(7-34) was inactive and hPTH(1-31) was fully active (Table 3, FIG. 9). Notably, maximal activation of u-PA secretion by hPTH (1-31) was identical to that of hPTH(1-34) even in HKRK B7 cells (FIG. 9, Table 3), where maximal PTH activity exceeds that achieved with maximal pharmacologic activation of PKA with 8BrcAMP, and in AB45 cells (FIG. 7), where PKA (and the action of 8BrcAMP) is almost completely blocked and the residual activity of PTH is presumably mediated almost entirely by PKA-independent signals. Similarly, in both HKRK B28 and HKRK B7 cells, hPTH (1-31) and hPTH(1-34) (as well as hPTHrP(1-36)) showed comparable maximal activation of phosphate uptake, which is PKC-dependent in these cells (Guo, J., et al., *Endocrinology* 136:3884–3891 (1995)), whereas hPTH(3-34) and hPTH(7-34) were inactive, as expected (FIG. 8).

Table 3. Stimulation of u-PA Secretion by hPTH/PTHrp Peptides in HKRK B7 and HKRK B28 Cells Cells were incubated with the indicated peptides (1000 nM) for 16 hr before measurement of secreted u-PA present in the medium, which was expressed as a percentage of the activity measured in vehicle-treated controls. Values shown are means±SEM of triplicate determinations.

TABLE 3

| Peptide (1000 nM) | HKRK B7 | HKRK B28 |
| --- | --- | --- |
| hPTH (1–34) | 100 ± 5 | 100 ± 8 |
| hPTH (1–31) | 101 ± 9 | 101 ± 6 |
| hPTH (3–34) | 57 ± 3 | 50 ± 1 |
| hPTH (7–34) | 1 ± 1 | 0 ± 2 |
| hPTHrP (1–36) | 88 ± 5 | 97 ± 9 |

Figure 10:
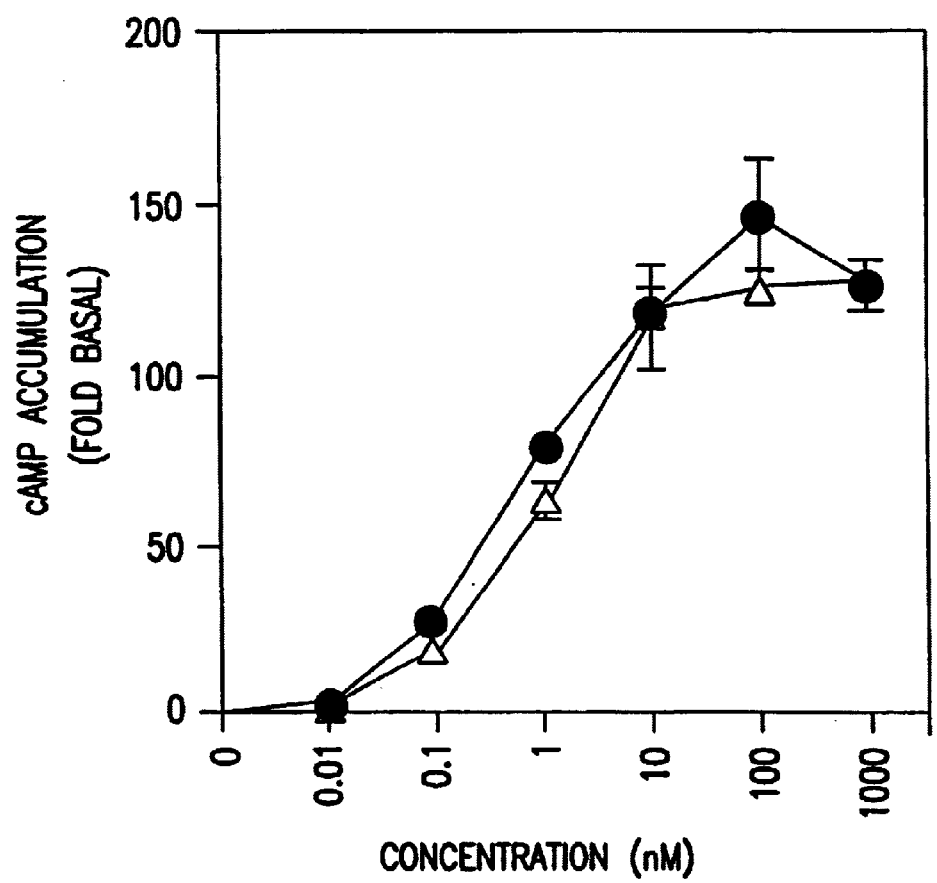
FIG. 10. Stimulation of cyclic AMP accumulation by hPTH(1-31) and hPTH(1-34) in LLC-PK1 cells that express rat PTHRs. Cyclic AMP accumulation was measured in response to hPTH(1-34) (●) or hPTH(1-31) (Δ) in EW5 cells that expressed 320,000 rat PTHRs per cell. Results are expressed as fold basal.

The full equivalence of the signaling and biologic properties of hPTH(1-31) and hPTH(1-34) that was observed via transfected human PTHRs in these LLC-PK1 cells was quite unexpected, as this analog has been reported to be devoid of activity in cellular bioassays of PKC activation, despite full potency with respect to stimulation of AC, in rat systems (Rixon, R. H., et al., *J Bone Miner Res* 9:1179–1189 (1994), Jouishomme, H., et al., *Endocrinology* 130:53–60 (1992), Neugebauer, W., et al., *Biochemistry* 34:8835–8842 (1995)). It was determined if the apparent discrepancy between the findings of the present inventors and the previous reports might relate to the difference in receptor species. Accordingly, the effects of hPTH(1-34) and hPTH(1-31) in LLC-PK1 cells (EW5) that express rat PTHRs were compared. Both peptides activated AC equivalently in EW 5 cells (FIG. 10). As shown in Table 4, maximal $IP_3$ generation by hPTH(1-31) via the rat PTHR in EW5 cells (and in 3 other rPTHR-expressing cell lines) was approximately 70% as great as that by hPTH(1-34), whereas u-PA production at 16 hr was identical in response to 100 nM of either peptide. Stimulation of phosphate uptake by the two peptides also was identical. Thus, the ability of hPTH(1-31) to activate PLC and other cAMP-independent responses via the PTHR was not restricted to the human receptor but was seen also in LLC-PK1 cells that express recombinant rat PTHRs. The PLC response to hPTH(1-31) may be modestly impaired, relative to hPTH(1-34), via the rat PTHR, whereas the human receptor seems unable to discriminate between these two ligands.

Table 4. Comparison of hPTH(1-34) and hPTH(1-31) in LLC-PK1 Cells Expressing Rat PTHR.

Responses to hPTH(1-34) or hPTH(1-31) (1000 nM) were measured in EW5 cells, which express 320,000 rat PTHRs per cell. Each value is the mean±SEM of a representative experiment performed in triplicate. Similar results were obtained in at least 3 individual experiments. The modest reduction in $IP_3$ formation observed with hPTH(1-31) relative to hPTH(1-34) was confirmed in 3 other LLC-PK1 cell lines that expressed rat PTHRs (i.e. EW29, AR-C38 and AR-B44, which express 190,000, 630,000 and 800,000 PTHRs/cell, respectively), in which maximal $IP_3$ formation after hPTH(1-31) (as % of hPTH(1-34) effect) was 75%, 77% and 64%, respectively.

TABLE 4

| Peptide (1000 nM) | $IP_3$ Formation (% of basal) | Phosphate uptake (% of basal) | u-PA Activity (units/well) |
| --- | --- | --- | --- |
| control | 100 ± 5 | 100 ± 2 | 0.8 ± 0.3 |
| hPTH (1–34) | 444 ± 31 | 130 ± 2 | 43.5 ± 1.8 |
| hPTH (1–31) | 316 ± 35 | 134 ± 3 | 41.2 ± 1.2 |

In view of the widely postulated linkage(s) between specific PTHR-generated second messenger signals and certain biologic actions of the hormone in tissues such as bone or kidney (Dempster, D. W., et al., *Endocrine Rev* 14:690–709 (1993), Rixon, R. H., et al., *J. Bone Miner Res* 9:1179–1189 (1994), Whitfield, J. F., and Morley, P., *Trends Pharmacol Sci* 16:382–386 (1995), Dunlay, R., and Hruska, K., *Am J. Physiol* 258:F223–231 (1990), Janulis, M., et al., *Endocrinology* 133:713–719 (1993)), it was of great interest to examine the properties of several truncated hPTH(1-34) analogs in cells expressing the human PTHR.

Weak but significant activation of AC (and u-PA secretion) by hPTH(3-34) but no PLC- or cytosolic calcium-stimulating activity was observed. These results contrast with other reports, based mainly in rodent models, in which PTH(3-34) peptides generally have exhibited loss of AC activation with relative preservation of PLC/PKC- or calcium-stimulating activity (Fujimori, A., et al., *Endocrinology* 128:3032–3039 (1991), Abou-Samra, A. B., et al., *Endocrinology* 135:2588–2594 (1994); Azarani A, et al., *J Biol Chem* 271:14931–14936 (1996); Chakravarthy, B. R., et al., *Biochem Biophys Res Commun* 171:1105–1110 (1990), Fujimori, A., et al., *Endocrinology* 130:29–36 (1992); Jouishomme, H., et al., *Endocrinology* 130:53–60 (1992); Janulis, M., et al., *Endocrinology* 133:713–719 (1993), Azarani, A., et al., *J Biol Chem* 270:23166–23172 (1995)). In transfected HEK 293 cells that expressed 400,000 human PTHRs per cell, Pines et al. observed slight but significant increases in both AC and cytosolic free calcium in response to 10 nM [Nle$^{8,18}$, Tyr$^{34}$]bPTH(3-34)amide (Pines, M., et al., *Bone* 18:381–389 (1996)), whereas no PLC or calcium responses to hPTH(3-34)amide at 100 nM was observed. On the other hand, others also have failed to detect activation of PKC or cytosolic calcium transients by PTH(3-34) peptides in rat and other non-human cell systems (Reid, I., et al., *Am J Physiol* 252:E45–E51 (1987); Civitelli, R., et al., *Endocrinology* 125:1204–1210 (1989); Tamura, T., et al., *Biochem Biophys Res Commun* 159:1352–1358 (1989)). It thus seems likely that these disparities may be attributable to differences in experimental systems or in the species and structure of the PTHRs involved or of the particular PTH(3-34) peptides employed.

More surprising was the finding that hPTH(1-31) was fully equivalent to hPTH(1-34) with respect to activation of AC, PLC, cytosolic calcium transients, u-PA secretion and phosphate uptake in LLC-PK1 cells that express hPTHRs. Previously, hPTH(1-31) had been reported to retain AC activity but to be devoid of PKC-stimulating activity (Rixon, R. H., et al., *J Bone Miner Res* 9:1179–1189 (1994), Jouishomme, H., et al., *J Bone Miner Res* 9:943–949 (1994), Neugebauer, W., et al., *Biochemistry* 34:8835–8842(1995)). These observations formed the basis of the proposal that the region hPTH(Jouishomme, H., et al., *J Bone Miner Res* 9:943–949 (1994), Schipani, E., et al., *Science* 268:98–100 (1995); Clegg, C. H., et al., *J Biol Chem* 262: 13111–13119 (1987); Menniti, F., et al., *Mol Pharmacol* 40:727–733 (1991); Fukayama, S., et al., *Endocrinology* 134:1851–1858 (1994)) comprises a core domain for activation of PKC via the PTHR (Whitfield, J. F., and Morley, P., *Trends Pharmacol Sci* 16:382–386 (1995), Jouishomme, H., et al., *J Bone Miner Res* 9:943–949 (1994)). Thus, experiments in which ovariectomized rats given daily injections of hPTH(1-31) exhibited increases in bone mass comparable to those seen with hPTH(1-34) have been widely interpreted as evidence of a primary role for the cAMP/PKA cascade in the anabolic effect of PTH on bone (Rixon, R. H., et al., *J Bone Miner Res* 9:1179–1189 (1994), Whitfield, J. F., et al., *Calcif Tissue Int* 58:81–87 (1996)). Although PKC was not measured directly, both a cytosolic calcium response to hPTH(1-31) that could not be mimicked by cAMP analogs and, as well, vigorous stimulation of phosphate uptake, a biologic response shown previously to be linked primarily to activation of PKC in these cells was observed(Guo, J., et al., *Endocrinology* 136:3884–3891 (1995)). Thus, the direct demonstration of PLC activation by hPTH(1-31) via the hPTHR is notable and raises the important possibility that the ligand selectivity of the human PTHR may differ substantially from that of the rat PTHR (given that all previous work had been conducted in rat systems). Such a conclusion would have important implications for efforts aimed at developing clinically useful signal-selective PTH analogs on the basis of bioassays in rats (Whitfield, J. F., and Morley, P., *Trends Pharmacol Sci* 16:382–386 (1995)).

To address this issue further, the activities of hPTH(1-34) and hPTH(1-31) in LLC-PK1 cells that expressed rat PTHRs were compared. Surprisingly, it was found that the activities of the two peptides are nearly indistinguishable in this system as well, although maximal PLC activation by hPTH (1-31) was reduced significantly—to 60% of the maximal response to hPTH(1-34). These findings are inconsistent with previous characterizations of hPTH(1-31) as a cAMP-selective analog in rat cells and indicate that the full range of cAMP-independent activities of hPTH(1-31) that were observed via hPTHRs in LLC-PK1 cells are not entirely unique to the human PTHR. Therefore, the difference in PTHR species per se would appear not to explain the disparity between the present findings in the HKRK cells and those previously reported by others using rat cells (Rixon, R. H., et al., *J Bone Miner Res* 9:1179–1189 (1994), Jouishomme, H., et al., *J Bone Miner Res* 9:943–949 (1994), Neugebauer, W., et al., *Biochemistry* 34:8835–8842 (1995)).

There are several possible explanations for the apparent differences between the present findings and those from previous investigations of the hPTH(1-31) peptide. First, different responses have been measured. PLC, cytosolic free calcium and certain distal biologic effects known to be linked to PLC/PKC activation in LLC-PK1 cells were measured, whereas Jouishomme et al. measured PKC in unextracted membranes but not PLC or cytosolic free calcium (Rixon, R. H., et al., *J Bone Miner Res* 9:1179–1189 (1994), Jouishomme, H., et al., *J Bone Miner Res* 9:943–949 (1994)). It is known that PKC may be regulated by upstream effectors other than PLC (Exton, J., *J Biol Chem* 265:1–4 (1990)). Second, previous work was conducted using ROS 17/2 osteosarcoma cells or primary cultures of rat splenic lymphocytes that express endogenous, rather than transfected, rat PTH receptor genes (Rixon, R. H., et al., *J Bone Miner Res* 9:1179–1189 (1994), Jouishomme, H., et al., *J Bone Miner Res* 9:943–949 (1994)). The ROS 17/2 cells almost certainly express the same rPTHR that were studied here, as they were the source of the ROS 17/2.8 subclone from which the rPTHR cDNA originally was cloned and then used to create the rPTHR-expressing LLC-PK1 cells used in the experiments (Abou-Samra, A. B., et al., *Proc Natl Acad Sci USA* 89:2732–2736 (1992), Bringhurst, F. R., et al., *Endocrinology* 132:2090–2098 (1993), Guo, J., et al., *Endocrinology* 136:3884–3891 (1995)). On the other hand, it is quite possible that ROS 17/2 cells and spleen cells express alternate species of receptors for PTH that could have influenced the response(s) to hPTH(1-31) in these cells. For example, a PTH receptor with apparent C-terminal specificity, not yet fully characterized, has been described in ROS 17/2.8 cells (Inomata, N., et al., *Endocrinology* 136:4732–4740). Third, the ROS 17/2 and rat spleen cell systems differ in other ways from the rPTHR-transfected LLC-PK1 cells that were studied: (a) the surface expression of PTHRs is known, or likely, to be lower than that in the LLC-PK1 cells were used, (b)

rPTHRs are coupled to rat rather than porcine G proteins, and (c) the relative quantities of the various subtypes of expressed G proteins and effector enzymes could be very different. The issue of lower PTHR expression may be particularly important. The data suggest that the potency of the hPTH(1-31) peptide for PLC/PKC activation via the rat PTHR is moderately reduced (by 40%), relative to that of hPTH(1-34). Given the important influence of receptor density upon PLC signaling that was described, it seems possible that this difference in potency for PLC between hPTH(1-34) and hPTH(1-31) could be amplified in cells that express fewer rPTHRs than do the LLC-PK1 cells used here. On the other hand, no loss of PLC-stimulating potency via the human PTHR for hPTH(1-31) was found, even in cells (HKRK B28) in which human PTHR surface density was close to the minimum required to detect this signal.

All references mentioned herein are incorporated by reference in the disclosure. Having now fully described the invention by way of illustration and example for purposes of clarity and understanding, it will be apparent to those of ordinary skill in the art that certain changes and modifications may be made in the disclosed embodiments and such modifications are intended to be within the scope of the present invention. As examples, the preferred embodiments constitute only one form of carrying out the claimed invention.

What is claimed is:

1. A method for determining whether a compound of interest is an agonist of a receptor which couples to both Gs and Gq proteins thereby affecting an adenylyl cyclase or phospholipase C pathway said method comprising:
   (a) introducing into a first and second cell line, an expression vector comprising a nucleotide sequence encoding said receptor which is not normally expressed in said first and second cell lines, wherein said first and second cell lines express urokinase-type plasminogen activator (u-PA) and said second cell line also has inhibited Gs signaling of u-PA activity relative to said first cell line;
   (b) contacting said first and second cell lines with said compound of interest;
   (c) measuring the u-PA activity by fluorescence or absorbance spectroscopy of the cell culture supernatant of step (b) and the cell culture supernatant of said first and second cell lines which have not been in contact with said compound of interest; and
   (d) determining whether said compound of interest is an agonist of a receptor which couples to both Gs and Gq proteins thereby affecting an adenylyl cyclase or phospholipase C pathway, wherein the u-PA activity of the supernatant from said first and second cell lines from step (b) is greater than the u-PA activity of the supernatant from said first and second cell lines which have not been in contact with said compound of interest.

2. The method of claim 1, wherein said Gs and Gq protein coupled receptor is human PTHR.

3. The method of claim 1, wherein said first cell line and said second cell line is LLC-PK1.

4. A method for determining whether a compound of interest is an agonist of a receptor which couples to both Gs and Gq proteins thereby affecting an adenylyl cyclase or phospholipase C pathway said method comprising:
   (a) providing a first and second cell line, wherein said first and second cell lines express urokinase-type plasminogen activator (u-PA) and wherein said second cell line also has inhibited Gs signaling of u-PA activity relative to said first cell line;
   (b) introducing into a group of said first and second cell lines, an expression vector comprising a nucleotide sequence encoding said receptor which is not normally expressed in said first and second cell lines, thereby providing stably transfected cells of said first and second cell lines;
   (c) contacting said stably transfected cells of step (b) and said first and second cell lines of step (a), which are not stably transfected with said receptor, with said compound;
   (d) measuring the u-PA activity, by fluorescence or absorbance spectroscopy, of the cell culture supernatant of said stably transfected cells of step (c) and the cell culture supernatant of said first and second cell lines of step (c); and
   (e) determining whether said compound of interest is an agonist of a receptor which couples to both Gs and Gq proteins thereby affecting an adenylyl cyclase or phospholipase C pathway, wherein the u-PA activity of the supernatant from said stably transfected cells of step (c) is greater than the u-PA activity of the supernatant of said first and second cell lines of step (c), which are not stably transfected with said receptor.

5. The method of claim 4, wherein said Gs and Gq protein coupled receptor is human PTHR.

6. The method of claim 4, wherein said first cell line and said second cell line is LLC-PK1.

7. A method for determining whether a compound of interest is an antagonist of a receptor which couples to both Gs and Gq proteins thereby affecting an adenylyl cyclase or phospholipase C pathway said method comprising:
   (a) introducing into a first and second cell line an expression vector comprising a nucleotide sequence encoding said receptor which is not normally expressed in said first and second cell lines, wherein said first and second cell lines express urokinase-type plasminogen activator (u-PA) and said second cell line also has inhibited Gs signaling of u-PA activity relative to said first cell line;
   (b) contacting a first group of said first and second cell lines of step (a) with a known agonist of said receptor;
   (c) contacting a second group of said first and second cell lines of step (a) with a known agonist of said receptor and said compound of interest;
   (d) measuring the u-PA activity, by fluorescence or absorbance spectroscopy, of the cell culture supernatant of said first and second groups of steps (b) and (c); and
   (e) determining whether said compound of interest is an antagonist of a receptor which couples to both Gs and Gq proteins thereby affecting an adenylyl cyclase or phospholipase C pathway, wherein the u-PA activity of the supernatant from said first group of step (b) is greater than the u-PA activity of the supernatant of said second group of step (c).

8. The method of claim 7, wherein said Gs and Gq protein coupled receptor is human PTHR.

9. The method of claim 7, wherein said first cell line and said second cell line is LLC-PK1.

10. The method of claim 7, wherein said compound of interest is administered after said agonist in step (c).

11. The method of claim 7, wherein said compound of interest is administered before said agonist in step (c).

12. The method of claim 7, wherein said compound of interest is administered concurrently as said agonist in step (c).

* * * * *

UNITED STATES PATENT AND TRADEMARK OFFICE
CERTIFICATE OF CORRECTION

PATENT NO.         : 7,033,773 B1
APPLICATION NO.    : 09/696982
DATED              : April 25, 2006
INVENTOR(S)        : Bringhurst et al.

It is certified that error appears in the above-identified patent and that said Letters Patent is hereby corrected as shown below:

Title Page, line 4, under ABSTRACT, replace "present-invention" with --present invention--.

Title Page 2, col. 1 line 9, under OTHER PUBLICATIONS, in Freyaldenhoven, A.M., et al., replace "modulaes" with --modulates--;

Col. 1 line 21, Under OTHER PUBLICATIONS, in Fukayama, S., et al., 1992, replace "SaOs-2" with --SaOS-2--.

Column 1, Line 45, replace "whitfield" with --Whitfield--.

Column 2, Line 28, replace "3639" with --3039--;

Line 63, replace "Endocinology" with --Endocrinology--.

Column 5, Line 41, replace "PTHR" with --PTHR.--.

Column 7, Line 27, replace "metallotionein" with --metallothionein--.

Column 8, Lines 20-21, replace "orestimating" with --or estimating--.

Column 10, Line 40, replace "arnide" with --amide--;

Line 49, replace "$Na_2HPO^4$" with --$Na_2HPO_4$ --;

Line 50, replace "isobtylmethylxanthine" with --isobutylmethylxanthine--.

Column 12, Line 25, replace "deterninant" with --determinant--.

Column 15, Line 34, replace "hPTMs" with --hPTHRs--;

Signed and Sealed this
Seventh Day of February, 2012

David J. Kappos
*Director of the United States Patent and Trademark Office*

Line 51, replace "(1995)) Similar" with -- (1995)). Similar--.

Column 16, Line 23, replace "(1996))" with --(1996)).--.

Column 17, Line 28, replace "were have observed" with --were observed--.

Column 22, Line 67, replace "cells were used" with --cells used--.